(12) United States Patent
Jones et al.

(10) Patent No.: US 9,858,668 B2
(45) Date of Patent: Jan. 2, 2018

(54) GUIDEWIRE ARTIFACT REMOVAL IN IMAGES

(71) Applicant: VOLCANO CORPORATION, San Diego, CA (US)

(72) Inventors: Jesse Jones, Billerica, MA (US); Elizabeth Begin, Billerica, MA (US); Anuja Nair, Bedford, MA (US); Jason Sproul, Watertown, MA (US)

(73) Assignee: VOLCANO CORPORATION, San Diego, CA (US)

( * ) Notice: Subject to any disclaimer, the term of this patent is extended or adjusted under 35 U.S.C. 154(b) by 411 days.

(21) Appl. No.: 14/044,968

(22) Filed: Oct. 3, 2013

(65) Prior Publication Data
US 2014/0100439 A1    Apr. 10, 2014

Related U.S. Application Data

(60) Provisional application No. 61/710,437, filed on Oct. 5, 2012.

(51) Int. Cl.
*A61B 5/05*    (2006.01)
*G06T 7/00*    (2017.01)
(Continued)

(52) U.S. Cl.
CPC .......... *G06T 7/0016* (2013.01); *A61B 5/0066* (2013.01); *A61B 5/0086* (2013.01); *A61B 5/02007* (2013.01); *A61B 5/6852* (2013.01); *A61B 8/12* (2013.01); *A61B 8/13* (2013.01); *A61B 8/5269* (2013.01); *G06T 5/002* (2013.01); *G06T 5/005* (2013.01); *G06T 5/50* (2013.01);
(Continued)

(58) Field of Classification Search
None
See application file for complete search history.

(56) References Cited

U.S. PATENT DOCUMENTS 3,301,258 A    1/1967    Werner
3,617,880 A    11/1971   Cormack et al.
(Continued)

FOREIGN PATENT DOCUMENTS

EP    1041373 A2    10/2000
EP    01172637 A1   1/2002
(Continued)

OTHER PUBLICATIONS

Bradley, Helen. "How to Replace a Face in Photoshop in 6 Easy Steps." Digital Photography School. Nov. 23, 2011. pp. 1-8. https://web.archive.org/web/20111123135652/http://www.digital-photography-school.com/how-to-replace-a-face-in-photoshop-in-6-easy-steps.*

(Continued)

*Primary Examiner* — James Kish

(57) ABSTRACT

This invention relates generally to methods and systems for removing an artifact within an image. Typically, the artifact is a guidewire artifact. In one aspect, at least two images of an imaging surface are acquired. Each acquired image comprises a set of data. A guidewire artifact is detected in one of the at least two images. The guidewire artifact is replaced with data representing the imaging surface obtained from another one of the at least two images. In certain embodiments, the at least two images are of the same imaging surface having a guidewire or object causing the artifact moved to a different position.

12 Claims, 13 Drawing Sheets

(51) Int. Cl.
*A61B 5/00* (2006.01)
*G06T 5/00* (2006.01)
*A61B 8/12* (2006.01)
*A61B 8/13* (2006.01)
*A61B 8/08* (2006.01)
*A61B 5/02* (2006.01)
*G06T 5/50* (2006.01)

(52) U.S. Cl.
CPC . *A61B 2576/02* (2013.01); *G06T 2207/10016* (2013.01); *G06T 2207/10101* (2013.01); *G06T 2207/10132* (2013.01); *G06T 2207/30021* (2013.01); *G06T 2207/30101* (2013.01)

(56) References Cited

U.S. PATENT DOCUMENTS

| | | |
|---|---|---|
| 3,789,841 A | 2/1974 | Antoshkiw |
| 3,841,308 A | 10/1974 | Tate |
| 4,140,364 A | 2/1979 | Yamashita et al. |
| 4,274,423 A | 6/1981 | Mizuno et al. |
| 4,344,438 A | 8/1982 | Schultz |
| 4,398,791 A | 8/1983 | Dorsey |
| 4,432,370 A | 2/1984 | Hughes et al. |
| 4,552,554 A | 11/1985 | Gould et al. |
| 4,577,543 A | 3/1986 | Wilson |
| 4,676,980 A | 6/1987 | Segal et al. |
| 4,682,895 A | 7/1987 | Costello |
| 4,733,665 A | 3/1988 | Palmaz |
| 4,744,619 A | 5/1988 | Cameron |
| 4,762,129 A | 8/1988 | Bonzel |
| 4,766,386 A | 8/1988 | Oliver et al. |
| 4,771,774 A | 9/1988 | Simpson et al. |
| 4,794,931 A | 1/1989 | Yock |
| 4,800,886 A | 1/1989 | Nestor |
| 4,803,639 A | 2/1989 | Steele et al. |
| 4,816,567 A | 3/1989 | Cabilly et al. |
| 4,819,740 A | 4/1989 | Warrington |
| 4,821,731 A | 4/1989 | Martinelli et al. |
| 4,824,435 A | 4/1989 | Giesy et al. |
| 4,830,023 A | 5/1989 | de Toledo et al. |
| 4,834,093 A | 5/1989 | Littleford et al. |
| 4,841,977 A | 6/1989 | Griffith et al. |
| 4,864,578 A | 9/1989 | Proffitt et al. |
| 4,873,690 A | 10/1989 | Adams |
| 4,877,314 A | 10/1989 | Kanamori |
| 4,887,606 A | 12/1989 | Yock et al. |
| 4,917,085 A | 4/1990 | Smith |
| 4,917,097 A | 4/1990 | Proudian et al. |
| 4,928,693 A | 5/1990 | Goodin et al. |
| 4,932,413 A | 6/1990 | Shockey et al. |
| 4,932,419 A | 6/1990 | de Toledo |
| 4,948,229 A | 8/1990 | Soref |
| 4,951,677 A | 8/1990 | Crowley et al. |
| 4,969,742 A | 11/1990 | Falk et al. |
| 4,987,412 A | 1/1991 | Vaitekunas et al. |
| 4,993,412 A | 2/1991 | Murphy-Chutorian |
| 4,998,972 A | 3/1991 | Chin et al. |
| 5,000,185 A | 3/1991 | Yock |
| 5,024,234 A | 6/1991 | Leary et al. |
| 5,025,445 A | 6/1991 | Anderson et al. |
| 5,032,123 A | 7/1991 | Katz et al. |
| 5,037,169 A | 8/1991 | Chun |
| 5,039,193 A | 8/1991 | Snow et al. |
| 5,040,548 A | 8/1991 | Yock |
| 5,041,108 A | 8/1991 | Fox et al. |
| 5,054,492 A | 10/1991 | Scribner et al. |
| 5,065,010 A | 11/1991 | Knute |
| 5,065,769 A | 11/1991 | de Toledo |
| 5,085,221 A | 2/1992 | Ingebrigtsen et al. |
| 5,095,911 A | 3/1992 | Pomeranz |
| 5,100,424 A | 3/1992 | Jang et al. |
| 5,120,308 A | 6/1992 | Hess |
| 5,125,137 A | 6/1992 | Corl et al. |
| 5,135,486 A | 8/1992 | Eberle et al. |
| 5,135,516 A | 8/1992 | Sahatjian et al. |
| 5,155,439 A | 10/1992 | Holmbo et al. |
| 5,158,548 A | 10/1992 | Lau et al. |
| 5,163,445 A | 11/1992 | Christian et al. |
| 5,167,233 A | 12/1992 | Eberle et al. |
| 5,174,295 A | 12/1992 | Christian et al. |
| 5,176,141 A | 1/1993 | Bom et al. |
| 5,176,674 A | 1/1993 | Hofmann |
| 5,178,159 A | 1/1993 | Christian |
| 5,183,048 A | 2/1993 | Eberle |
| 5,188,632 A | 2/1993 | Goldenberg |
| 5,201,316 A | 4/1993 | Pomeranz et al. |
| 5,202,745 A | 4/1993 | Sorin et al. |
| 5,203,779 A | 4/1993 | Muller et al. |
| 5,220,922 A | 6/1993 | Barany |
| 5,224,953 A | 7/1993 | Morgentaler |
| 5,226,421 A | 7/1993 | Frisbie et al. |
| 5,240,003 A | 8/1993 | Lancee et al. |
| 5,240,437 A | 8/1993 | Christian |
| 5,242,460 A | 9/1993 | Klein et al. |
| 5,243,988 A | 9/1993 | Sieben et al. |
| 5,257,974 A | 11/1993 | Cox |
| 5,266,302 A | 11/1993 | Peyman et al. |
| 5,267,954 A | 12/1993 | Nita |
| 5,301,001 A | 4/1994 | Murphy et al. |
| 5,312,425 A | 5/1994 | Evans et al. |
| 5,313,949 A | 5/1994 | Yock |
| 5,313,957 A | 5/1994 | Little |
| 5,319,492 A | 6/1994 | Dorn et al. |
| 5,321,501 A | 6/1994 | Swanson et al. |
| 5,325,198 A | 6/1994 | Hartley et al. |
| 5,336,178 A | 8/1994 | Kaplan et al. |
| 5,346,689 A | 9/1994 | Peyman et al. |
| 5,348,017 A | 9/1994 | Thornton et al. |
| 5,348,481 A | 9/1994 | Ortiz |
| 5,353,798 A | 10/1994 | Sieben |
| 5,358,409 A | 10/1994 | Obara |
| 5,358,478 A | 10/1994 | Thompson et al. |
| 5,368,037 A | 11/1994 | Eberle et al. |
| 5,373,845 A | 12/1994 | Gardineer et al. |
| 5,373,849 A | 12/1994 | Maroney et al. |
| 5,375,602 A | 12/1994 | Lancee et al. |
| 5,377,682 A | 1/1995 | Ueno et al. |
| 5,383,853 A | 1/1995 | Jung et al. |
| 5,387,193 A | 2/1995 | Miraki |
| 5,396,328 A | 3/1995 | Jestel et al. |
| 5,397,355 A | 3/1995 | Marin et al. |
| 5,405,377 A | 4/1995 | Cragg |
| 5,411,016 A | 5/1995 | Kume et al. |
| 5,419,777 A | 5/1995 | Hofling |
| 5,421,338 A | 6/1995 | Crowley et al. |
| 5,423,806 A | 6/1995 | Dale et al. |
| 5,427,118 A | 6/1995 | Nita et al. |
| 5,431,673 A | 7/1995 | Summers et al. |
| 5,436,759 A | 7/1995 | Dijaili et al. |
| 5,439,139 A | 8/1995 | Brovelli |
| 5,443,457 A | 8/1995 | Ginn et al. |
| 5,453,575 A | 9/1995 | O'Donnell et al. |
| 5,456,693 A | 10/1995 | Conston et al. |
| 5,459,570 A | 10/1995 | Swanson et al. |
| 5,480,388 A | 1/1996 | Zadini et al. |
| 5,485,845 A | 1/1996 | Verdonk et al. |
| 5,492,125 A | 2/1996 | Kim et al. |
| 5,496,997 A | 3/1996 | Pope |
| 5,507,761 A | 4/1996 | Duer |
| 5,512,044 A | 4/1996 | Duer |
| 5,514,128 A | 5/1996 | Hillsman et al. |
| 5,529,674 A | 6/1996 | Hedgcoth |
| 5,541,730 A | 7/1996 | Chaney |
| 5,546,717 A | 8/1996 | Penczak et al. |
| 5,546,948 A | 8/1996 | Hamm et al. |
| 5,565,332 A | 10/1996 | Hoogenboom et al. |
| 5,573,520 A | 11/1996 | Schwartz et al. |
| 5,581,638 A | 12/1996 | Givens et al. |
| 5,586,054 A | 12/1996 | Jensen et al. |
| 5,592,939 A | 1/1997 | Martinelli |
| 5,596,079 A | 1/1997 | Smith et al. |
| 5,598,844 A | 2/1997 | Diaz et al. |
| 5,609,606 A | 3/1997 | O'Boyle |

(56) References Cited

U.S. PATENT DOCUMENTS

| | | |
|---|---|---|
| 5,630,806 A | 5/1997 | Inagaki et al. |
| 5,651,366 A | 7/1997 | Liang et al. |
| 5,660,180 A | 8/1997 | Malinowski et al. |
| 5,667,499 A | 9/1997 | Welch et al. |
| 5,667,521 A | 9/1997 | Keown |
| 5,672,877 A | 9/1997 | Liebig et al. |
| 5,674,232 A | 10/1997 | Halliburton |
| 5,693,015 A | 12/1997 | Walker et al. |
| 5,713,848 A | 2/1998 | Dubrul et al. |
| 5,745,634 A | 4/1998 | Garrett et al. |
| 5,771,895 A | 6/1998 | Slager |
| 5,779,731 A | 7/1998 | Leavitt |
| 5,780,958 A | 7/1998 | Strugach et al. |
| 5,798,521 A | 8/1998 | Froggatt |
| 5,800,450 A | 9/1998 | Lary et al. |
| 5,803,083 A | 9/1998 | Buck et al. |
| 5,814,061 A | 9/1998 | Osborne et al. |
| 5,817,025 A | 10/1998 | Alekseev et al. |
| 5,820,594 A | 10/1998 | Fontirroche et al. |
| 5,824,520 A | 10/1998 | Mulligan-Kehoe |
| 5,827,313 A | 10/1998 | Ream |
| 5,830,222 A | 11/1998 | Makower |
| 5,848,121 A | 12/1998 | Gupta et al. |
| 5,851,464 A | 12/1998 | Davila et al. |
| 5,857,974 A | 1/1999 | Eberle et al. |
| 5,872,829 A | 2/1999 | Wischmann et al. |
| 5,873,835 A | 2/1999 | Hastings et al. |
| 5,882,722 A | 3/1999 | Kydd |
| 5,912,764 A | 6/1999 | Togino |
| 5,916,194 A | 6/1999 | Jacobsen et al. |
| 5,921,931 A | 7/1999 | O'Donnell et al. |
| 5,925,055 A | 7/1999 | Adrian et al. |
| 5,949,929 A | 9/1999 | Hamm |
| 5,951,586 A | 9/1999 | Berg et al. |
| 5,974,521 A | 10/1999 | Akerib |
| 5,976,120 A | 11/1999 | Chow et al. |
| 5,978,391 A | 11/1999 | Das et al. |
| 5,997,523 A | 12/1999 | Jang |
| 6,021,240 A | 2/2000 | Murphy et al. |
| 6,022,319 A | 2/2000 | Willard et al. |
| 6,031,071 A | 2/2000 | Mandeville et al. |
| 6,036,889 A | 3/2000 | Kydd |
| 6,043,883 A | 3/2000 | Leckel et al. |
| 6,050,949 A | 4/2000 | White et al. |
| 6,059,738 A | 5/2000 | Stoltze et al. |
| 6,068,638 A | 5/2000 | Makower |
| 6,074,362 A | 6/2000 | Jang et al. |
| 6,078,831 A | 6/2000 | Belef et al. |
| 6,080,109 A | 6/2000 | Baker et al. |
| 6,091,496 A | 7/2000 | Hill |
| 6,094,591 A | 7/2000 | Foltz et al. |
| 6,095,976 A | 8/2000 | Nachtomy et al. |
| 6,097,755 A | 8/2000 | Guenther, Jr. et al. |
| 6,099,471 A | 8/2000 | Torp et al. |
| 6,099,549 A | 8/2000 | Bosma et al. |
| 6,102,938 A | 8/2000 | Evans et al. |
| 6,106,476 A | 8/2000 | Corl et al. |
| 6,120,445 A | 9/2000 | Grunwald |
| 6,123,673 A | 9/2000 | Eberle et al. |
| 6,134,003 A | 10/2000 | Tearney et al. |
| 6,139,510 A | 10/2000 | Palermo |
| 6,141,089 A | 10/2000 | Thoma et al. |
| 6,146,328 A | 11/2000 | Chiao et al. |
| 6,148,095 A | 11/2000 | Prause et al. |
| 6,151,433 A | 11/2000 | Dower et al. |
| 6,152,877 A | 11/2000 | Masters |
| 6,152,878 A | 11/2000 | Nachtomy et al. |
| 6,159,225 A | 12/2000 | Makower |
| 6,165,127 A | 12/2000 | Crowley |
| 6,176,842 B1 | 1/2001 | Tachibana et al. |
| 6,179,809 B1 | 1/2001 | Khairkhahan et al. |
| 6,186,949 B1 | 2/2001 | Hatfield et al. |
| 6,190,353 B1 | 2/2001 | Makower et al. |
| 6,200,266 B1 | 3/2001 | Shokrollahi et al. |
| 6,200,268 B1 | 3/2001 | Vince et al. |
| 6,203,537 B1 | 3/2001 | Adrian |
| 6,208,415 B1 | 3/2001 | De Boer et al. |
| 6,210,332 B1 | 4/2001 | Chiao et al. |
| 6,210,339 B1 | 4/2001 | Kiepen et al. |
| 6,212,308 B1 | 4/2001 | Donald |
| 6,231,518 B1 | 5/2001 | Grabek et al. |
| 6,245,066 B1 | 6/2001 | Morgan et al. |
| 6,249,076 B1 | 6/2001 | Madden et al. |
| 6,254,543 B1 | 7/2001 | Grunwald et al. |
| 6,256,090 B1 | 7/2001 | Chen et al. |
| 6,258,052 B1 | 7/2001 | Milo |
| 6,261,246 B1 | 7/2001 | Pantages et al. |
| 6,275,628 B1 | 8/2001 | Jones et al. |
| 6,283,921 B1 | 9/2001 | Nix et al. |
| 6,283,951 B1 | 9/2001 | Flaherty et al. |
| 6,295,308 B1 | 9/2001 | Zah |
| 6,299,622 B1 | 10/2001 | Snow et al. |
| 6,312,384 B1 | 11/2001 | Chiao |
| 6,325,797 B1 | 12/2001 | Stewart et al. |
| 6,328,696 B1 | 12/2001 | Fraser |
| 6,343,168 B1 | 1/2002 | Murphy et al. |
| 6,343,178 B1 | 1/2002 | Burns et al. |
| 6,350,240 B1 | 2/2002 | Song et al. |
| 6,364,841 B1 | 4/2002 | White et al. |
| 6,366,722 B1 | 4/2002 | Murphy et al. |
| 6,367,984 B1 | 4/2002 | Stephenson et al. |
| 6,373,970 B1 | 4/2002 | Dong et al. |
| 6,375,615 B1 | 4/2002 | Flaherty et al. |
| 6,375,618 B1 | 4/2002 | Chiao et al. |
| 6,375,628 B1 | 4/2002 | Zadno-Azizi et al. |
| 6,376,830 B1 | 4/2002 | Froggatt et al. |
| 6,379,352 B1 | 4/2002 | Reynolds et al. |
| 6,381,350 B1 | 4/2002 | Klingensmith et al. |
| 6,387,124 B1 | 5/2002 | Buscemi et al. |
| 6,396,976 B1 | 5/2002 | Little et al. |
| 6,398,792 B1 | 6/2002 | O'Connor |
| 6,417,948 B1 | 7/2002 | Chowdhury et al. |
| 6,419,644 B1 | 7/2002 | White et al. |
| 6,421,164 B2 | 7/2002 | Tearney et al. |
| 6,423,012 B1 | 7/2002 | Kato et al. |
| 6,426,796 B1 | 7/2002 | Pulliam et al. |
| 6,428,041 B1 | 8/2002 | Wohllebe et al. |
| 6,428,498 B2 | 8/2002 | Uflacker |
| 6,429,421 B1 | 8/2002 | Meller et al. |
| 6,440,077 B1 | 8/2002 | Jung et al. |
| 6,443,903 B1 | 9/2002 | White et al. |
| 6,450,964 B1 | 9/2002 | Webler |
| 6,457,365 B1 | 10/2002 | Stephens et al. |
| 6,459,844 B1 | 10/2002 | Pan |
| 6,468,290 B1 | 10/2002 | Weldon et al. |
| 6,475,149 B1 | 11/2002 | Sumanaweera |
| 6,480,285 B1 | 11/2002 | Hill |
| 6,491,631 B2 | 12/2002 | Chiao et al. |
| 6,491,636 B2 | 12/2002 | Chenal et al. |
| 6,501,551 B1 | 12/2002 | Tearney et al. |
| 6,504,286 B1 | 1/2003 | Porat et al. |
| 6,508,824 B1 | 1/2003 | Flaherty et al. |
| 6,514,237 B1 | 2/2003 | Maseda |
| 6,520,269 B2 | 2/2003 | Geiger et al. |
| 6,520,677 B2 | 2/2003 | Iizuka |
| 6,535,764 B2 | 3/2003 | Imran et al. |
| 6,538,778 B1 | 3/2003 | Leckel et al. |
| 6,544,217 B1 | 4/2003 | Gulachenski |
| 6,544,230 B1 | 4/2003 | Flaherty et al. |
| 6,545,760 B1 | 4/2003 | Froggatt et al. |
| 6,546,272 B1 | 4/2003 | MacKinnon et al. |
| 6,551,250 B2 | 4/2003 | Khalil |
| 6,566,648 B1 | 5/2003 | Froggatt |
| 6,570,894 B2 | 5/2003 | Anderson |
| 6,572,555 B2 | 6/2003 | White et al. |
| 6,579,311 B1 | 6/2003 | Makower |
| 6,584,335 B1 | 6/2003 | Haar et al. |
| 6,592,612 B1 | 7/2003 | Samson et al. |
| 6,594,448 B2 | 7/2003 | Herman et al. |
| 6,602,241 B2 | 8/2003 | Makower et al. |
| 6,611,322 B1 | 8/2003 | Nakayama et al. |
| 6,611,720 B2 | 8/2003 | Hata et al. |
| 6,612,992 B1 | 9/2003 | Hossack et al. |
| 6,615,062 B2 | 9/2003 | Ryan et al. |

(56) References Cited

U.S. PATENT DOCUMENTS

| | | |
|---|---|---|
| 6,615,072 B1 | 9/2003 | Izatt et al. |
| 6,621,562 B2 | 9/2003 | Durston |
| 6,631,284 B2 | 10/2003 | Nutt et al. |
| 6,638,227 B2 | 10/2003 | Bae |
| 6,645,152 B1 | 11/2003 | Jung et al. |
| 6,646,745 B2 | 11/2003 | Verma et al. |
| 6,655,386 B1 | 12/2003 | Makower et al. |
| 6,659,957 B1 | 12/2003 | Vardi et al. |
| 6,660,024 B1 | 12/2003 | Flaherty et al. |
| 6,663,565 B2 | 12/2003 | Kawagishi et al. |
| 6,665,456 B2 | 12/2003 | Dave et al. |
| 6,669,716 B1 | 12/2003 | Gilson et al. |
| 6,671,055 B1 | 12/2003 | Wavering et al. |
| 6,673,015 B1 | 1/2004 | Glover et al. |
| 6,673,064 B1 | 1/2004 | Rentrop |
| 6,685,648 B2 | 2/2004 | Flaherty et al. |
| 6,689,056 B1 | 2/2004 | Kilcoyne et al. |
| 6,689,144 B2 | 2/2004 | Gerberding |
| 6,696,173 B1 | 2/2004 | Naundorf et al. |
| 6,701,044 B2 | 3/2004 | Arbore et al. |
| 6,701,176 B1 | 3/2004 | Halperin et al. |
| 6,709,444 B1 | 3/2004 | Makower |
| 6,712,836 B1 | 3/2004 | Berg et al. |
| 6,714,703 B2 | 3/2004 | Lee et al. |
| 6,719,717 B1 | 4/2004 | Johnson et al. |
| 6,725,073 B1 | 4/2004 | Motamedi et al. |
| 6,726,677 B1 | 4/2004 | Flaherty et al. |
| 6,730,107 B2 | 5/2004 | Kelley et al. |
| 6,733,474 B2 | 5/2004 | Kusleika |
| 6,738,144 B1 | 5/2004 | Dogariu |
| 6,740,113 B2 | 5/2004 | Vrba |
| 6,746,464 B1 | 6/2004 | Makower |
| 6,780,157 B2 | 8/2004 | Stephens et al. |
| 6,795,188 B2 | 9/2004 | Ruck et al. |
| 6,795,196 B2 | 9/2004 | Funakawa |
| 6,798,522 B2 | 9/2004 | Stolte et al. |
| 6,822,798 B2 | 11/2004 | Wu et al. |
| 6,830,559 B2 | 12/2004 | Schock |
| 6,832,024 B2 | 12/2004 | Gerstenberger et al. |
| 6,842,639 B1 | 1/2005 | Winston et al. |
| 6,847,449 B2 | 1/2005 | Bashkansky et al. |
| 6,855,115 B2 | 2/2005 | Fonseca et al. |
| 6,856,138 B2 | 2/2005 | Bohley |
| 6,856,400 B1 | 2/2005 | Froggatt |
| 6,856,472 B2 | 2/2005 | Herman et al. |
| 6,860,867 B2 | 3/2005 | Seward et al. |
| 6,866,670 B2 | 3/2005 | Rabiner et al. |
| 6,878,113 B2 | 4/2005 | Miwa et al. |
| 6,886,411 B2 | 5/2005 | Kjellman et al. |
| 6,891,984 B2 | 5/2005 | Petersen et al. |
| 6,895,106 B2 | 5/2005 | Wang et al. |
| 6,898,337 B2 | 5/2005 | Averett et al. |
| 6,900,897 B2 | 5/2005 | Froggatt |
| 6,912,051 B2 | 6/2005 | Jensen |
| 6,916,329 B1 | 7/2005 | Zhao |
| 6,922,498 B2 | 7/2005 | Shah |
| 6,937,346 B2 | 8/2005 | Nebendahl et al. |
| 6,937,696 B1 | 8/2005 | Mostafavi |
| 6,943,939 B1 | 9/2005 | DiJaili et al. |
| 6,947,147 B2 | 9/2005 | Motamedi et al. |
| 6,947,787 B2 | 9/2005 | Webler |
| 6,949,094 B2 | 9/2005 | Yaron |
| 6,952,603 B2 | 10/2005 | Gerber et al. |
| 6,954,737 B2 | 10/2005 | Kalantar et al. |
| 6,958,042 B2 | 10/2005 | Honda |
| 6,961,123 B1 | 11/2005 | Wang et al. |
| 6,966,891 B2 | 11/2005 | Ookubo et al. |
| 6,969,293 B2 | 11/2005 | Thai |
| 6,969,395 B2 | 11/2005 | Eskuri |
| 6,985,234 B2 | 1/2006 | Anderson |
| 7,004,963 B2 | 2/2006 | Wang et al. |
| 7,006,231 B2 | 2/2006 | Ostrovsky et al. |
| 7,010,458 B2 | 3/2006 | Wilt |
| 7,024,025 B2 | 4/2006 | Sathyanarayana |
| 7,027,211 B1 | 4/2006 | Ruffa |
| 7,027,743 B1 | 4/2006 | Tucker et al. |
| 7,033,347 B2 | 4/2006 | Appling |
| 7,035,484 B2 | 4/2006 | Silberberg et al. |
| 7,037,269 B2 | 5/2006 | Nix et al. |
| 7,042,573 B2 | 5/2006 | Froggatt |
| 7,044,915 B2 | 5/2006 | White et al. |
| 7,044,964 B2 | 5/2006 | Jang et al. |
| 7,048,711 B2 | 5/2006 | Rosenman et al. |
| 7,049,306 B2 | 5/2006 | Konradi et al. |
| 7,058,239 B2 | 6/2006 | Singh et al. |
| 7,060,033 B2 | 6/2006 | White et al. |
| 7,060,421 B2 | 6/2006 | Naundorf et al. |
| 7,063,679 B2 | 6/2006 | Maguire et al. |
| 7,068,852 B2 | 6/2006 | Braica |
| 7,074,188 B2 | 7/2006 | Nair et al. |
| 7,095,493 B2 | 8/2006 | Harres |
| 7,110,119 B2 | 9/2006 | Maestle |
| 7,113,875 B2 | 9/2006 | Terashima et al. |
| 7,123,777 B2 | 10/2006 | Rondinelli et al. |
| 7,130,054 B2 | 10/2006 | Ostrovsky et al. |
| 7,139,440 B2 | 11/2006 | Rondinelli et al. |
| 7,153,299 B1 | 12/2006 | Tu et al. |
| 7,171,078 B2 | 1/2007 | Sasaki et al. |
| 7,175,597 B2 | 2/2007 | Vince et al. |
| 7,177,491 B2 | 2/2007 | Dave et al. |
| 7,190,464 B2 | 3/2007 | Alphonse |
| 7,215,802 B2 | 5/2007 | Klingensmith et al. |
| 7,218,811 B2 | 5/2007 | Shigenaga et al. |
| 7,236,812 B1 | 6/2007 | Ballerstadt et al. |
| 7,245,125 B2 | 7/2007 | Harer et al. |
| 7,245,789 B2 | 7/2007 | Bates et al. |
| 7,249,357 B2 | 7/2007 | Landman et al. |
| 7,291,146 B2 | 11/2007 | Steinke et al. |
| 7,292,715 B2 | 11/2007 | Furnish |
| 7,292,885 B2 | 11/2007 | Scott et al. |
| 7,294,124 B2 | 11/2007 | Eidenschink |
| 7,300,460 B2 | 11/2007 | Levine et al. |
| 7,335,161 B2 | 2/2008 | Von Arx et al. |
| 7,337,079 B2 | 2/2008 | Park et al. |
| 7,355,716 B2 | 4/2008 | de Boer et al. |
| 7,356,367 B2 | 4/2008 | Liang et al. |
| 7,358,921 B2 | 4/2008 | Snyder et al. |
| 7,359,062 B2 | 4/2008 | Chen et al. |
| 7,359,554 B2 | 4/2008 | Klingensmith et al. |
| 7,363,927 B2 | 4/2008 | Ravikumar |
| 7,366,376 B2 | 4/2008 | Shishkov et al. |
| 7,382,949 B2 | 6/2008 | Bouma et al. |
| 7,387,636 B2 | 6/2008 | Cohn et al. |
| 7,391,520 B2 | 6/2008 | Zhou et al. |
| 7,397,935 B2 | 7/2008 | Kimmel et al. |
| 7,399,095 B2 | 7/2008 | Rondinelli |
| 7,408,648 B2 | 8/2008 | Kleen et al. |
| 7,414,779 B2 | 8/2008 | Huber et al. |
| 7,440,087 B2 | 10/2008 | Froggatt et al. |
| 7,447,388 B2 | 11/2008 | Bates et al. |
| 7,449,821 B2 | 11/2008 | Dausch |
| 7,450,165 B2 | 11/2008 | Ahiska |
| RE40,608 E | 12/2008 | Glover et al. |
| 7,458,967 B2 | 12/2008 | Appling et al. |
| 7,463,362 B2 | 12/2008 | Lasker et al. |
| 7,463,759 B2 | 12/2008 | Klingensmith et al. |
| 7,491,226 B2 | 2/2009 | Palmaz et al. |
| 7,515,276 B2 | 4/2009 | Froggatt et al. |
| 7,527,594 B2 | 5/2009 | Vardi et al. |
| 7,534,251 B2 | 5/2009 | WasDyke |
| 7,535,797 B2 | 5/2009 | Peng et al. |
| 7,547,304 B2 | 6/2009 | Johnson |
| 7,564,949 B2 | 7/2009 | Sattler et al. |
| 7,577,471 B2 | 8/2009 | Camus et al. |
| 7,583,857 B2 | 9/2009 | Xu et al. |
| 7,603,165 B2 | 10/2009 | Townsend et al. |
| 7,612,773 B2 | 11/2009 | Magnin et al. |
| 7,633,627 B2 | 12/2009 | Choma et al. |
| 7,645,229 B2 | 1/2010 | Armstrong |
| 7,658,715 B2 | 2/2010 | Park et al. |
| 7,660,452 B2 | 2/2010 | Zwirn et al. |
| 7,660,492 B2 | 2/2010 | Bates et al. |
| 7,666,204 B2 | 2/2010 | Thornton et al. |
| 7,672,790 B2 | 3/2010 | McGraw et al. |

(56) References Cited

U.S. PATENT DOCUMENTS

| | | |
|---|---|---|
| 7,680,247 B2 | 3/2010 | Atzinger et al. |
| 7,684,991 B2 | 3/2010 | Stohr et al. |
| 7,711,413 B2 | 5/2010 | Feldman et al. |
| 7,720,322 B2 | 5/2010 | Prisco |
| 7,728,986 B2 | 6/2010 | Lasker et al. |
| 7,734,009 B2 | 6/2010 | Brunner et al. |
| 7,736,317 B2 | 6/2010 | Stephens et al. |
| 7,742,795 B2 | 6/2010 | Stone et al. |
| 7,743,189 B2 | 6/2010 | Brown et al. |
| 7,762,954 B2 | 7/2010 | Nix et al. |
| 7,766,896 B2 | 8/2010 | Kornkven Volk et al. |
| 7,773,792 B2 | 8/2010 | Kimmel et al. |
| 7,775,981 B1 | 8/2010 | Guracar et al. |
| 7,777,399 B2 | 8/2010 | Eidenschink et al. |
| 7,781,724 B2 | 8/2010 | Childers et al. |
| 7,783,337 B2 | 8/2010 | Feldman et al. |
| 7,787,127 B2 | 8/2010 | Galle et al. |
| 7,792,342 B2 | 9/2010 | Barbu et al. |
| 7,801,343 B2 | 9/2010 | Unal et al. |
| 7,801,590 B2 | 9/2010 | Feldman et al. |
| 7,813,609 B2 | 10/2010 | Petersen et al. |
| 7,831,081 B2 | 11/2010 | Li |
| 7,846,101 B2 | 12/2010 | Eberle et al. |
| 7,853,104 B2 | 12/2010 | Oota et al. |
| 7,853,316 B2 | 12/2010 | Milner et al. |
| 7,860,555 B2 | 12/2010 | Saadat |
| 7,862,508 B2 | 1/2011 | Davies et al. |
| 7,872,759 B2 | 1/2011 | Tearney et al. |
| 7,880,868 B2 | 2/2011 | Aoki |
| 7,881,763 B2 | 2/2011 | Brauker et al. |
| 7,909,844 B2 | 3/2011 | Alkhatib et al. |
| 7,921,854 B2 | 4/2011 | Hennings et al. |
| 7,927,784 B2 | 4/2011 | Simpson |
| 7,929,148 B2 | 4/2011 | Kemp |
| 7,930,014 B2 | 4/2011 | Huennekens et al. |
| 7,930,104 B2 | 4/2011 | Baker et al. |
| 7,936,462 B2 | 5/2011 | Jiang et al. |
| 7,942,852 B2 | 5/2011 | Mas et al. |
| 7,947,012 B2 | 5/2011 | Spurchise et al. |
| 7,951,186 B2 | 5/2011 | Eidenschink et al. |
| 7,952,719 B2 | 5/2011 | Brennan, III |
| 7,972,353 B2 | 7/2011 | Hendriksen et al. |
| 7,976,492 B2 | 7/2011 | Brauker et al. |
| 7,977,950 B2 | 7/2011 | Maslen |
| 7,978,916 B2 | 7/2011 | Klingensmith et al. |
| 7,981,041 B2 | 7/2011 | McGahan |
| 7,981,151 B2 | 7/2011 | Rowe |
| 7,983,737 B2 | 7/2011 | Feldman et al. |
| 7,993,333 B2 | 8/2011 | Oral et al. |
| 7,995,210 B2 | 8/2011 | Tearney et al. |
| 7,996,060 B2 | 8/2011 | Trofimov et al. |
| 7,999,938 B2 | 8/2011 | Wang |
| 8,021,377 B2 | 9/2011 | Eskuri |
| 8,021,420 B2 | 9/2011 | Dolan |
| 8,036,732 B2 | 10/2011 | Milner |
| 8,040,586 B2 | 10/2011 | Smith et al. |
| 8,047,996 B2 | 11/2011 | Goodnow et al. |
| 8,049,900 B2 | 11/2011 | Kemp et al. |
| 8,050,478 B2 | 11/2011 | Li et al. |
| 8,050,523 B2 | 11/2011 | Younge et al. |
| 8,052,605 B2 | 11/2011 | Muller et al. |
| 8,057,394 B2 | 11/2011 | Dala-Krishna |
| 8,059,923 B2 | 11/2011 | Bates et al. |
| 8,070,800 B2 | 12/2011 | Lock et al. |
| 8,080,800 B2 | 12/2011 | Hoctor et al. |
| 8,088,102 B2 | 1/2012 | Adams et al. |
| 8,100,838 B2 | 1/2012 | Wright et al. |
| 8,104,479 B2 | 1/2012 | Glynn et al. |
| 8,108,030 B2 | 1/2012 | Castella et al. |
| 8,114,102 B2 | 2/2012 | Galdonik et al. |
| 8,116,605 B2 | 2/2012 | Petersen et al. |
| 8,125,648 B2 | 2/2012 | Milner et al. |
| 8,126,239 B2 | 2/2012 | Sun et al. |
| 8,133,199 B2 | 3/2012 | Weber et al. |
| 8,133,269 B2 | 3/2012 | Flechsenhar et al. |
| 8,140,708 B2 | 3/2012 | Zaharia et al. |
| 8,148,877 B2 | 4/2012 | Jiang et al. |
| 8,167,932 B2 | 5/2012 | Bourang et al. |
| 8,172,757 B2 | 5/2012 | Jaffe et al. |
| 8,177,809 B2 | 5/2012 | Mavani et al. |
| 8,187,191 B2 | 5/2012 | Hancock et al. |
| 8,187,267 B2 | 5/2012 | Pappone et al. |
| 8,187,830 B2 | 5/2012 | Hu et al. |
| 8,199,218 B2 | 6/2012 | Lee et al. |
| 8,206,429 B2 | 6/2012 | Gregorich et al. |
| 8,208,995 B2 | 6/2012 | Tearney et al. |
| 8,222,906 B2 | 7/2012 | Wyar et al. |
| 8,233,681 B2 | 7/2012 | Aylward et al. |
| 8,233,718 B2 | 7/2012 | Klingensmith et al. |
| 8,238,624 B2 | 8/2012 | Doi et al. |
| 8,239,938 B2 | 8/2012 | Simeral et al. |
| 8,277,386 B2 | 10/2012 | Ahmed et al. |
| 8,280,470 B2 | 10/2012 | Milner et al. |
| 8,289,284 B2 | 10/2012 | Glynn et al. |
| 8,289,522 B2 | 10/2012 | Tearney et al. |
| 8,298,147 B2 | 10/2012 | Huennekens et al. |
| 8,298,149 B2 | 10/2012 | Hastings et al. |
| 8,301,000 B2 | 10/2012 | Sillard et al. |
| 8,309,428 B2 | 11/2012 | Lemmerhirt et al. |
| 8,317,713 B2 | 11/2012 | Davies et al. |
| 8,323,201 B2 | 12/2012 | Towfiq et al. |
| 8,329,053 B2 | 12/2012 | Martin et al. |
| 8,336,643 B2 | 12/2012 | Harleman |
| 8,349,000 B2 | 1/2013 | Schreck |
| 8,353,945 B2 | 1/2013 | Andreas et al. |
| 8,353,954 B2 | 1/2013 | Cai et al. |
| 8,357,981 B2 | 1/2013 | Martin et al. |
| 8,361,097 B2 | 1/2013 | Patel et al. |
| 8,386,560 B2 | 2/2013 | Ma et al. |
| 8,398,591 B2 | 3/2013 | Mas et al. |
| 8,412,312 B2 | 4/2013 | Judell et al. |
| 8,417,491 B2 | 4/2013 | Trovato et al. |
| 8,449,465 B2 | 5/2013 | Nair et al. |
| 8,454,685 B2 | 6/2013 | Hariton et al. |
| 8,454,686 B2 | 6/2013 | Alkhatib |
| 8,475,522 B2 | 7/2013 | Jimenez et al. |
| 8,478,384 B2 | 7/2013 | Schmitt et al. |
| 8,486,062 B2 | 7/2013 | Belhe et al. |
| 8,486,063 B2 | 7/2013 | Werneth et al. |
| 8,491,567 B2 | 7/2013 | Magnin et al. |
| 8,500,798 B2 | 8/2013 | Rowe et al. |
| 8,509,604 B2 | 8/2013 | Wright et al. |
| 8,550,911 B2 | 10/2013 | Sylla |
| 8,594,757 B2 | 11/2013 | Boppart et al. |
| 8,597,349 B2 | 12/2013 | Alkhatib |
| 8,600,477 B2 | 12/2013 | Beyar et al. |
| 8,600,917 B1 | 12/2013 | Schimert et al. |
| 8,601,056 B2 | 12/2013 | Lauwers et al. |
| 8,620,055 B2 | 12/2013 | Barratt et al. |
| 8,644,910 B2 | 2/2014 | Rousso et al. |
| 2001/0007940 A1 | 7/2001 | Tu et al. |
| 2001/0029337 A1 | 10/2001 | Pantages et al. |
| 2001/0031920 A1 | 10/2001 | Kaufman et al. |
| 2001/0037073 A1 | 11/2001 | White et al. |
| 2001/0046345 A1 | 11/2001 | Snyder et al. |
| 2001/0049548 A1 | 12/2001 | Vardi et al. |
| 2002/0034276 A1 | 3/2002 | Hu et al. |
| 2002/0041723 A1 | 4/2002 | Ronneklivi et al. |
| 2002/0069676 A1 | 6/2002 | Kopp et al. |
| 2002/0089335 A1 | 7/2002 | Williams |
| 2002/0099289 A1 | 7/2002 | Crowley |
| 2002/0163646 A1 | 11/2002 | Anderson |
| 2002/0186818 A1 | 12/2002 | Arnaud et al. |
| 2002/0196446 A1 | 12/2002 | Roth et al. |
| 2002/0197456 A1 | 12/2002 | Pope |
| 2003/0004412 A1 | 1/2003 | Izatt et al. |
| 2003/0016604 A1 | 1/2003 | Hanes |
| 2003/0018273 A1 | 1/2003 | Corl et al. |
| 2003/0023153 A1 | 1/2003 | Izatt et al. |
| 2003/0032886 A1 | 2/2003 | Dgany et al. |
| 2003/0050871 A1 | 3/2003 | Broughton |
| 2003/0065371 A1 | 4/2003 | Satake |
| 2003/0069723 A1 | 4/2003 | Hegde |
| 2003/0077043 A1 | 4/2003 | Hamm et al. |

(56) References Cited

U.S. PATENT DOCUMENTS

| | | |
|---|---|---|
| 2003/0085635 A1 | 5/2003 | Davidsen |
| 2003/0090753 A1 | 5/2003 | Takeyama et al. |
| 2003/0092995 A1 | 5/2003 | Thompson |
| 2003/0093059 A1 | 5/2003 | Griffin et al. |
| 2003/0103212 A1 | 6/2003 | Westphal et al. |
| 2003/0152259 A1 | 8/2003 | Belykh et al. |
| 2003/0181802 A1 | 9/2003 | Ogawa |
| 2003/0187369 A1 | 10/2003 | Lewis et al. |
| 2003/0194165 A1 | 10/2003 | Silberberg et al. |
| 2003/0195419 A1 | 10/2003 | Harada |
| 2003/0208116 A1 | 11/2003 | Liang et al. |
| 2003/0212491 A1 | 11/2003 | Mitchell et al. |
| 2003/0219202 A1 | 11/2003 | Loeb et al. |
| 2003/0220749 A1 | 11/2003 | Chen et al. |
| 2003/0228039 A1 | 12/2003 | Green |
| 2004/0015065 A1 | 1/2004 | Panescu et al. |
| 2004/0023317 A1 | 2/2004 | Motamedi et al. |
| 2004/0028333 A1 | 2/2004 | Lomas |
| 2004/0037742 A1 | 2/2004 | Jen et al. |
| 2004/0042066 A1 | 3/2004 | Kinoshita et al. |
| 2004/0054287 A1 | 3/2004 | Stephens |
| 2004/0067000 A1 | 4/2004 | Bates et al. |
| 2004/0068161 A1 | 4/2004 | Couvillon |
| 2004/0082844 A1 | 4/2004 | Vardi et al. |
| 2004/0092830 A1 | 5/2004 | Scott et al. |
| 2004/0106853 A1 | 6/2004 | Moriyama |
| 2004/0111552 A1 | 6/2004 | Arimilli et al. |
| 2004/0126048 A1 | 7/2004 | Dave et al. |
| 2004/0143160 A1 | 7/2004 | Couvillon |
| 2004/0146546 A1 | 7/2004 | Gravett et al. |
| 2004/0186369 A1 | 9/2004 | Lam |
| 2004/0186558 A1 | 9/2004 | Pavcnik et al. |
| 2004/0195512 A1 | 10/2004 | Crosetto |
| 2004/0220606 A1 | 11/2004 | Goshgarian |
| 2004/0225220 A1 | 11/2004 | Rich |
| 2004/0239938 A1 | 12/2004 | Izatt |
| 2004/0242990 A1 | 12/2004 | Brister et al. |
| 2004/0248439 A1 | 12/2004 | Gernhardt et al. |
| 2004/0260236 A1 | 12/2004 | Manning et al. |
| 2005/0013778 A1 | 1/2005 | Green et al. |
| 2005/0031176 A1 | 2/2005 | Hertel et al. |
| 2005/0036150 A1 | 2/2005 | Izatt et al. |
| 2005/0078317 A1 | 4/2005 | Law et al. |
| 2005/0101859 A1 | 5/2005 | Maschke |
| 2005/0140582 A1 | 6/2005 | Lee et al. |
| 2005/0140682 A1 | 6/2005 | Sumanaweera et al. |
| 2005/0140981 A1 | 6/2005 | Waelti |
| 2005/0140984 A1 | 6/2005 | Hitzenberger |
| 2005/0147303 A1 | 7/2005 | Zhou et al. |
| 2005/0165439 A1 | 7/2005 | Weber et al. |
| 2005/0171433 A1 | 8/2005 | Boppart et al. |
| 2005/0171438 A1 | 8/2005 | Chen et al. |
| 2005/0182297 A1 | 8/2005 | Gravenstein et al. |
| 2005/0196028 A1 | 9/2005 | Kleen et al. |
| 2005/0197585 A1 | 9/2005 | Brockway et al. |
| 2005/0213103 A1 | 9/2005 | Everett et al. |
| 2005/0215942 A1 | 9/2005 | Abrahamson et al. |
| 2005/0234445 A1 | 10/2005 | Conquergood et al. |
| 2005/0243322 A1 | 11/2005 | Lasker et al. |
| 2005/0249391 A1* | 11/2005 | Kimmel .................. G06T 7/143 382/128 |
| 2005/0251567 A1 | 11/2005 | Ballew et al. |
| 2005/0254059 A1 | 11/2005 | Alphonse |
| 2005/0264823 A1 | 12/2005 | Zhu et al. |
| 2006/0013523 A1 | 1/2006 | Childers et al. |
| 2006/0015126 A1 | 1/2006 | Sher |
| 2006/0029634 A1 | 2/2006 | Berg et al. |
| 2006/0036167 A1 | 2/2006 | Shina |
| 2006/0038115 A1 | 2/2006 | Maas |
| 2006/0039004 A1 | 2/2006 | de Boer et al. |
| 2006/0041180 A1 | 2/2006 | Viswanathan et al. |
| 2006/0045536 A1 | 3/2006 | Arahira |
| 2006/0055936 A1 | 3/2006 | Yun et al. |
| 2006/0058622 A1 | 3/2006 | Tearney et al. |
| 2006/0064009 A1 | 3/2006 | Webler et al. |
| 2006/0067620 A1 | 3/2006 | Shishkov et al. |
| 2006/0072808 A1 | 4/2006 | Grimm et al. |
| 2006/0074442 A1 | 4/2006 | Noriega et al. |
| 2006/0098927 A1 | 5/2006 | Schmidt et al. |
| 2006/0100694 A1 | 5/2006 | Globerman |
| 2006/0106375 A1 | 5/2006 | Werneth et al. |
| 2006/0132790 A1 | 6/2006 | Gutin |
| 2006/0135870 A1 | 6/2006 | Webler |
| 2006/0142703 A1 | 6/2006 | Carter et al. |
| 2006/0142733 A1 | 6/2006 | Forsberg |
| 2006/0173299 A1 | 8/2006 | Romley et al. |
| 2006/0179255 A1 | 8/2006 | Yamazaki |
| 2006/0184048 A1 | 8/2006 | Saadat |
| 2006/0187537 A1 | 8/2006 | Huber et al. |
| 2006/0195269 A1 | 8/2006 | Yeatman et al. |
| 2006/0204119 A1 | 9/2006 | Feng et al. |
| 2006/0229591 A1 | 10/2006 | Lee |
| 2006/0239312 A1 | 10/2006 | Kewitsch et al. |
| 2006/0241342 A1 | 10/2006 | Macaulay et al. |
| 2006/0241465 A1 | 10/2006 | Huennekens et al. |
| 2006/0241503 A1 | 10/2006 | Schmitt et al. |
| 2006/0244973 A1 | 11/2006 | Yun et al. |
| 2006/0253024 A1 | 11/2006 | Altmann et al. |
| 2006/0258895 A1 | 11/2006 | Maschke |
| 2006/0264743 A1 | 11/2006 | Kleen et al. |
| 2006/0267756 A1 | 11/2006 | Kates |
| 2006/0270976 A1 | 11/2006 | Savage et al. |
| 2006/0276709 A1 | 12/2006 | Khamene et al. |
| 2006/0279742 A1 | 12/2006 | Tearney et al. |
| 2006/0279743 A1 | 12/2006 | Boesser et al. |
| 2006/0285638 A1 | 12/2006 | Boese et al. |
| 2006/0287595 A1 | 12/2006 | Maschke |
| 2006/0293597 A1 | 12/2006 | Johnson et al. |
| 2007/0015969 A1 | 1/2007 | Feldman et al. |
| 2007/0016029 A1 | 1/2007 | Donaldson et al. |
| 2007/0016034 A1 | 1/2007 | Donaldson |
| 2007/0016062 A1 | 1/2007 | Park et al. |
| 2007/0027390 A1 | 2/2007 | Maschke et al. |
| 2007/0036417 A1 | 2/2007 | Argiro et al. |
| 2007/0038061 A1 | 2/2007 | Huennekens et al. |
| 2007/0038121 A1 | 2/2007 | Feldman et al. |
| 2007/0038125 A1 | 2/2007 | Kleen et al. |
| 2007/0043292 A1 | 2/2007 | Camus et al. |
| 2007/0043597 A1 | 2/2007 | Donaldson |
| 2007/0049847 A1 | 3/2007 | Osborne |
| 2007/0060973 A1 | 3/2007 | Ludvig et al. |
| 2007/0065077 A1 | 3/2007 | Childers et al. |
| 2007/0066888 A1 | 3/2007 | Maschke |
| 2007/0066890 A1 | 3/2007 | Maschke |
| 2007/0066983 A1 | 3/2007 | Maschke |
| 2007/0083101 A1* | 4/2007 | Rietzel .......................... 600/407 |
| 2007/0084995 A1 | 4/2007 | Newton et al. |
| 2007/0100226 A1 | 5/2007 | Yankelevitz et al. |
| 2007/0135887 A1 | 6/2007 | Maschke |
| 2007/0142707 A1 | 6/2007 | Wiklof et al. |
| 2007/0156019 A1 | 7/2007 | Larkin et al. |
| 2007/0161893 A1 | 7/2007 | Milner et al. |
| 2007/0161896 A1 | 7/2007 | Adachi et al. |
| 2007/0161963 A1 | 7/2007 | Smalling |
| 2007/0162860 A1 | 7/2007 | Muralidharan et al. |
| 2007/0165141 A1 | 7/2007 | Srinivas et al. |
| 2007/0167710 A1* | 7/2007 | Unal ...................... A61B 5/0066 600/407 |
| 2007/0167804 A1 | 7/2007 | Park et al. |
| 2007/0191682 A1 | 8/2007 | Rolland et al. |
| 2007/0201736 A1 | 8/2007 | Klingensmith et al. |
| 2007/0206193 A1 | 9/2007 | Pesach |
| 2007/0208276 A1 | 9/2007 | Kornkven Volk et al. |
| 2007/0225220 A1 | 9/2007 | Ming et al. |
| 2007/0225590 A1 | 9/2007 | Ramos |
| 2007/0229801 A1 | 10/2007 | Tearney et al. |
| 2007/0232872 A1 | 10/2007 | Prough et al. |
| 2007/0232874 A1 | 10/2007 | Ince |
| 2007/0232890 A1 | 10/2007 | Hirota |
| 2007/0232891 A1 | 10/2007 | Hirota |
| 2007/0232892 A1 | 10/2007 | Hirota |
| 2007/0232893 A1 | 10/2007 | Tanioka |
| 2007/0232933 A1 | 10/2007 | Gille et al. |
| 2007/0238957 A1 | 10/2007 | Yared |

(56) References Cited

U.S. PATENT DOCUMENTS

| | | |
|---|---|---|
| 2007/0247033 A1 | 10/2007 | Eidenschink et al. |
| 2007/0250000 A1 | 10/2007 | Magnin et al. |
| 2007/0250036 A1 | 10/2007 | Volk et al. |
| 2007/0258094 A1 | 11/2007 | Izatt et al. |
| 2007/0260138 A1 | 11/2007 | Feldman et al. |
| 2007/0278389 A1 | 12/2007 | Ajgaonkar et al. |
| 2007/0287914 A1 | 12/2007 | Cohen |
| 2008/0002183 A1 | 1/2008 | Yatagai et al. |
| 2008/0013093 A1 | 1/2008 | Izatt et al. |
| 2008/0021275 A1 | 1/2008 | Tearney et al. |
| 2008/0027481 A1 | 1/2008 | Gilson et al. |
| 2008/0043024 A1 | 2/2008 | Schiwietz et al. |
| 2008/0045842 A1 | 2/2008 | Furnish |
| 2008/0051660 A1 | 2/2008 | Kakadaris et al. |
| 2008/0063304 A1 | 3/2008 | Russak et al. |
| 2008/0085041 A1 | 4/2008 | Breeuwer |
| 2008/0095465 A1 | 4/2008 | Mullick et al. |
| 2008/0095714 A1 | 4/2008 | Castella et al. |
| 2008/0097194 A1 | 4/2008 | Milner |
| 2008/0101667 A1 | 5/2008 | Begelman et al. |
| 2008/0108867 A1 | 5/2008 | Zhou |
| 2008/0114254 A1 | 5/2008 | Matcovitch et al. |
| 2008/0119739 A1 | 5/2008 | Vardi et al. |
| 2008/0124495 A1 | 5/2008 | Horn et al. |
| 2008/0125772 A1 | 5/2008 | Stone et al. |
| 2008/0139897 A1 | 6/2008 | Ainsworth et al. |
| 2008/0143707 A1 | 6/2008 | Mitchell |
| 2008/0146941 A1 | 6/2008 | Dala-Krishna |
| 2008/0147111 A1 | 6/2008 | Johnson et al. |
| 2008/0154128 A1 | 6/2008 | Milner |
| 2008/0161696 A1 | 7/2008 | Schmitt et al. |
| 2008/0171944 A1 | 7/2008 | Brenneman et al. |
| 2008/0175465 A1 | 7/2008 | Jiang et al. |
| 2008/0177183 A1* | 7/2008 | Courtney ............ A61B 5/0062 600/463 |
| 2008/0180683 A1 | 7/2008 | Kemp |
| 2008/0181477 A1 | 7/2008 | Izatt et al. |
| 2008/0187201 A1 | 8/2008 | Liang et al. |
| 2008/0228086 A1 | 9/2008 | Ilegbusi et al. |
| 2008/0247622 A1 | 10/2008 | Aylward et al. |
| 2008/0247716 A1 | 10/2008 | Thomas et al. |
| 2008/0262470 A1 | 10/2008 | Lee et al. |
| 2008/0262489 A1 | 10/2008 | Steinke |
| 2008/0269599 A1 | 10/2008 | Csavoy et al. |
| 2008/0281205 A1 | 11/2008 | Naghavi et al. |
| 2008/0281248 A1 | 11/2008 | Angheloiu et al. |
| 2008/0285043 A1 | 11/2008 | Fercher et al. |
| 2008/0287795 A1 | 11/2008 | Klingensmith et al. |
| 2008/0291463 A1 | 11/2008 | Milner et al. |
| 2008/0292173 A1 | 11/2008 | Hsieh et al. |
| 2008/0294034 A1 | 11/2008 | Krueger et al. |
| 2008/0298655 A1 | 12/2008 | Edwards |
| 2008/0306766 A1 | 12/2008 | Ozeki et al. |
| 2009/0009801 A1 | 1/2009 | Tabuki |
| 2009/0018393 A1 | 1/2009 | Dick et al. |
| 2009/0034813 A1 | 2/2009 | Dikmen et al. |
| 2009/0043191 A1 | 2/2009 | Castella et al. |
| 2009/0046295 A1 | 2/2009 | Kemp et al. |
| 2009/0052614 A1 | 2/2009 | Hempel et al. |
| 2009/0069843 A1 | 3/2009 | Agnew |
| 2009/0079993 A1 | 3/2009 | Yatagai et al. |
| 2009/0088650 A1 | 4/2009 | Corl |
| 2009/0093980 A1 | 4/2009 | Kemp et al. |
| 2009/0122320 A1 | 5/2009 | Petersen et al. |
| 2009/0138544 A1 | 5/2009 | Wegenkittl et al. |
| 2009/0149739 A9 | 6/2009 | Maschke |
| 2009/0156941 A1 | 6/2009 | Moore |
| 2009/0174886 A1 | 7/2009 | Inoue |
| 2009/0174931 A1 | 7/2009 | Huber et al. |
| 2009/0177090 A1 | 7/2009 | Grunwald et al. |
| 2009/0177183 A1 | 7/2009 | Pinkernell et al. |
| 2009/0195514 A1 | 8/2009 | Glynn et al. |
| 2009/0196470 A1 | 8/2009 | Carl et al. |
| 2009/0198125 A1 | 8/2009 | Nakabayashi et al. |
| 2009/0203991 A1 | 8/2009 | Papaioannou et al. |
| 2009/0264768 A1 | 10/2009 | Courtney et al. |
| 2009/0269014 A1 | 10/2009 | Winberg et al. |
| 2009/0270695 A1 | 10/2009 | Mceowen |
| 2009/0284322 A1 | 11/2009 | Harrison et al. |
| 2009/0284332 A1 | 11/2009 | Moore et al. |
| 2009/0284749 A1 | 11/2009 | Johnson et al. |
| 2009/0290167 A1 | 11/2009 | Flanders et al. |
| 2009/0292048 A1 | 11/2009 | Li et al. |
| 2009/0299195 A1 | 12/2009 | Muller et al. |
| 2009/0299284 A1 | 12/2009 | Holman et al. |
| 2009/0318951 A1 | 12/2009 | Kashkarov et al. |
| 2009/0326634 A1 | 12/2009 | Vardi |
| 2010/0007669 A1 | 1/2010 | Bethune et al. |
| 2010/0030042 A1 | 2/2010 | Denninghoff et al. |
| 2010/0061611 A1 | 3/2010 | Xu et al. |
| 2010/0063400 A1 | 3/2010 | Hall et al. |
| 2010/0087732 A1 | 4/2010 | Eberle et al. |
| 2010/0094125 A1 | 4/2010 | Younge et al. |
| 2010/0094127 A1 | 4/2010 | Xu |
| 2010/0094135 A1 | 4/2010 | Fang-Yen et al. |
| 2010/0094143 A1 | 4/2010 | Mahapatra et al. |
| 2010/0113919 A1 | 5/2010 | Maschke |
| 2010/0125238 A1 | 5/2010 | Lye et al. |
| 2010/0125268 A1 | 5/2010 | Gustus et al. |
| 2010/0125648 A1 | 5/2010 | Zaharia et al. |
| 2010/0128348 A1 | 5/2010 | Taverner |
| 2010/0152717 A1 | 6/2010 | Keeler |
| 2010/0160788 A1 | 6/2010 | Davies et al. |
| 2010/0161023 A1 | 6/2010 | Cohen et al. |
| 2010/0168714 A1 | 7/2010 | Burke et al. |
| 2010/0179421 A1 | 7/2010 | Tupin |
| 2010/0179426 A1 | 7/2010 | Davies et al. |
| 2010/0220334 A1 | 9/2010 | Condit et al. |
| 2010/0226607 A1 | 9/2010 | Zhang et al. |
| 2010/0234736 A1 | 9/2010 | Corl |
| 2010/0249601 A1 | 9/2010 | Courtney |
| 2010/0256616 A1 | 10/2010 | Katoh et al. |
| 2010/0272432 A1 | 10/2010 | Johnson |
| 2010/0284590 A1 | 11/2010 | Peng et al. |
| 2010/0290693 A1 | 11/2010 | Cohen et al. |
| 2010/0331950 A1 | 12/2010 | Strommer |
| 2011/0010925 A1 | 1/2011 | Nix et al. |
| 2011/0021926 A1 | 1/2011 | Spencer et al. |
| 2011/0025853 A1 | 2/2011 | Richardson |
| 2011/0026797 A1 | 2/2011 | Declerck et al. |
| 2011/0032533 A1 | 2/2011 | Izatt et al. |
| 2011/0034801 A1 | 2/2011 | Baumgart |
| 2011/0044546 A1 | 2/2011 | Pan et al. |
| 2011/0066073 A1 | 3/2011 | Kuiper et al. |
| 2011/0071401 A1 | 3/2011 | Hastings et al. |
| 2011/0071404 A1* | 3/2011 | Schmitt et al. ............ 600/479 |
| 2011/0072405 A1 | 3/2011 | Chen et al. |
| 2011/0077528 A1 | 3/2011 | Kemp et al. |
| 2011/0080591 A1 | 4/2011 | Johnson et al. |
| 2011/0087104 A1* | 4/2011 | Moore .................... A61B 8/12 600/447 |
| 2011/0137140 A1 | 6/2011 | Tearney et al. |
| 2011/0144502 A1 | 6/2011 | Zhou et al. |
| 2011/0152771 A1 | 6/2011 | Milner et al. |
| 2011/0157597 A1 | 6/2011 | Lu et al. |
| 2011/0160586 A1 | 6/2011 | Li et al. |
| 2011/0178413 A1 | 7/2011 | Schmitt et al. |
| 2011/0190586 A1 | 8/2011 | Kemp |
| 2011/0216378 A1 | 9/2011 | Poon et al. |
| 2011/0220985 A1 | 9/2011 | Son et al. |
| 2011/0229056 A1* | 9/2011 | Robertson et al. ........... 382/294 |
| 2011/0238061 A1 | 9/2011 | van der Weide et al. |
| 2011/0238083 A1 | 9/2011 | Moll et al. |
| 2011/0245669 A1 | 10/2011 | Zhang |
| 2011/0249094 A1 | 10/2011 | Wang et al. |
| 2011/0257545 A1 | 10/2011 | Suri |
| 2011/0264125 A1 | 10/2011 | Wilson et al. |
| 2011/0274329 A1 | 11/2011 | Mathew et al. |
| 2011/0282334 A1 | 11/2011 | Groenhoff |
| 2011/0301684 A1 | 12/2011 | Fischell et al. |
| 2011/0306995 A1 | 12/2011 | Moberg |
| 2011/0319752 A1 | 12/2011 | Steinberg et al. |
| 2012/0004529 A1 | 1/2012 | Tolkowsky et al. |
| 2012/0004668 A1 | 1/2012 | Wallace et al. |

(56) References Cited

U.S. PATENT DOCUMENTS

| | | |
|---|---|---|
| 2012/0013914 A1 | 1/2012 | Kemp et al. |
| 2012/0016344 A1 | 1/2012 | Kusakabe |
| 2012/0016395 A1 | 1/2012 | Olson |
| 2012/0022360 A1 | 1/2012 | Kemp |
| 2012/0026503 A1 | 2/2012 | Lewandowski et al. |
| 2012/0029007 A1 | 2/2012 | Graham et al. |
| 2012/0059253 A1 | 3/2012 | Wang et al. |
| 2012/0059368 A1 | 3/2012 | Takaoka et al. |
| 2012/0062843 A1 | 3/2012 | Ferguson et al. |
| 2012/0065481 A1 | 3/2012 | Hunter et al. |
| 2012/0071823 A1 | 3/2012 | Chen |
| 2012/0071838 A1 | 3/2012 | Fojtik |
| 2012/0075638 A1 | 3/2012 | Rollins et al. |
| 2012/0083696 A1 | 4/2012 | Kitamura |
| 2012/0095340 A1 | 4/2012 | Smith |
| 2012/0095372 A1 | 4/2012 | Sverdlik et al. |
| 2012/0108943 A1 | 5/2012 | Bates et al. |
| 2012/0113108 A1 | 5/2012 | Dala-Krishna |
| 2012/0116353 A1 | 5/2012 | Arnold et al. |
| 2012/0130243 A1 | 5/2012 | Balocco et al. |
| 2012/0130247 A1 | 5/2012 | Waters et al. |
| 2012/0136259 A1 | 5/2012 | Milner et al. |
| 2012/0136427 A1 | 5/2012 | Palmaz et al. |
| 2012/0137075 A1 | 5/2012 | Vorbach |
| 2012/0155734 A1 | 6/2012 | Barratt et al. |
| 2012/0158101 A1 | 6/2012 | Stone et al. |
| 2012/0162660 A1 | 6/2012 | Kemp |
| 2012/0165661 A1 | 6/2012 | Kemp et al. |
| 2012/0170848 A1 | 7/2012 | Kemp et al. |
| 2012/0172698 A1 | 7/2012 | Teo et al. |
| 2012/0176607 A1 | 7/2012 | Ott |
| 2012/0184853 A1 | 7/2012 | Waters |
| 2012/0184859 A1 | 7/2012 | Shah et al. |
| 2012/0184977 A1 | 7/2012 | Wolf |
| 2012/0215094 A1 | 8/2012 | Rahimian et al. |
| 2012/0220836 A1 | 8/2012 | Alpert et al. |
| 2012/0220851 A1 | 8/2012 | Razansky et al. |
| 2012/0220865 A1 | 8/2012 | Brown et al. |
| 2012/0220874 A1 | 8/2012 | Hancock et al. |
| 2012/0220883 A1 | 8/2012 | Manstrom et al. |
| 2012/0224751 A1 | 9/2012 | Kemp et al. |
| 2012/0226153 A1 | 9/2012 | Brown et al. |
| 2012/0230565 A1 | 9/2012 | Steinberg et al. |
| 2012/0232400 A1 | 9/2012 | Dickinson et al. |
| 2012/0238869 A1 | 9/2012 | Schmitt et al. |
| 2012/0238956 A1 | 9/2012 | Yamada et al. |
| 2012/0244043 A1 | 9/2012 | Leblanc et al. |
| 2012/0250028 A1 | 10/2012 | Schmitt et al. |
| 2012/0253186 A1 | 10/2012 | Simpson et al. |
| 2012/0253192 A1 | 10/2012 | Cressman |
| 2012/0253276 A1 | 10/2012 | Govari et al. |
| 2012/0257210 A1 | 10/2012 | Whitney et al. |
| 2012/0262720 A1 | 10/2012 | Brown et al. |
| 2012/0265077 A1 | 10/2012 | Gille et al. |
| 2012/0265268 A1 | 10/2012 | Blum et al. |
| 2012/0265296 A1 | 10/2012 | McNamara et al. |
| 2012/0271170 A1 | 10/2012 | Emelianov et al. |
| 2012/0271175 A1 | 10/2012 | Moore et al. |
| 2012/0271339 A1 | 10/2012 | O'Beirne et al. |
| 2012/0274338 A1 | 11/2012 | Baks et al. |
| 2012/0276390 A1 | 11/2012 | Ji et al. |
| 2012/0277722 A1 | 11/2012 | Gerber et al. |
| 2012/0279764 A1 | 11/2012 | Jiang et al. |
| 2012/0283758 A1 | 11/2012 | Miller et al. |
| 2012/0289987 A1 | 11/2012 | Wilson et al. |
| 2012/0299439 A1 | 11/2012 | Huang |
| 2012/0310081 A1 | 12/2012 | Adler et al. |
| 2012/0310332 A1 | 12/2012 | Murray et al. |
| 2012/0319535 A1 | 12/2012 | Dausch |
| 2012/0323075 A1 | 12/2012 | Younge et al. |
| 2012/0323127 A1 | 12/2012 | Boyden et al. |
| 2012/0330141 A1 | 12/2012 | Brown et al. |
| 2013/0004065 A1* | 1/2013 | Ma ................... 382/165 |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0026655 A1 | 1/2013 | Lee et al. |
| 2013/0030295 A1 | 1/2013 | Huennekens et al. |
| 2013/0030303 A1 | 1/2013 | Ahmed et al. |
| 2013/0030410 A1 | 1/2013 | Drasler et al. |
| 2013/0053949 A1 | 2/2013 | Pintor et al. |
| 2013/0076941 A1* | 3/2013 | Palanciuc et al. ....... 348/231.99 |
| 2013/0109958 A1 | 5/2013 | Baumgart et al. |
| 2013/0109959 A1 | 5/2013 | Baumgart et al. |
| 2013/0137980 A1 | 5/2013 | Waters et al. |
| 2013/0150716 A1 | 6/2013 | Stigall et al. |
| 2013/0158594 A1 | 6/2013 | Carrison et al. |
| 2013/0216114 A1 | 8/2013 | Courtney et al. |
| 2013/0218201 A1 | 8/2013 | Obermiller et al. |
| 2013/0218267 A1 | 8/2013 | Braido et al. |
| 2013/0223789 A1 | 8/2013 | Lee et al. |
| 2013/0223798 A1 | 8/2013 | Jenner et al. |
| 2013/0271728 A1* | 10/2013 | Ranchod ................... 351/206 |
| 2013/0296704 A1 | 11/2013 | Magnin et al. |
| 2013/0303907 A1 | 11/2013 | Corl |
| 2013/0303920 A1 | 11/2013 | Corl |
| 2013/0310698 A1 | 11/2013 | Judell et al. |
| 2013/0331820 A1 | 12/2013 | Itou et al. |
| 2013/0338766 A1 | 12/2013 | Hastings et al. |
| 2013/0339958 A1 | 12/2013 | Droste et al. |
| 2014/0039294 A1 | 2/2014 | Jiang |
| 2014/0180067 A1 | 6/2014 | Stigall et al. |
| 2014/0180128 A1 | 6/2014 | Corl |
| 2014/0200438 A1 | 7/2014 | Millett et al. |

FOREIGN PATENT DOCUMENTS

| | | |
|---|---|---|
| EP | 2438877 A2 | 4/2012 |
| GB | 2280261 A | 1/1995 |
| JP | 2000-262461 A | 9/2000 |
| JP | 2000-292260 A | 10/2000 |
| JP | 2001-125009 A | 5/2001 |
| JP | 2001-272331 A | 10/2001 |
| JP | 2002-374034 A | 12/2002 |
| JP | 2003-143783 A | 5/2003 |
| JP | 2003-172690 A | 6/2003 |
| JP | 2003-256876 A | 9/2003 |
| JP | 2003-287534 A | 10/2003 |
| JP | 2005-274380 A | 10/2005 |
| JP | 2006-184284 A | 7/2006 |
| JP | 2006-266797 A | 10/2006 |
| JP | 2006-313158 A | 11/2006 |
| JP | 2007-024677 A | 2/2007 |
| JP | 2009-233001 A | 10/2009 |
| JP | 2011-56786 A | 3/2011 |
| WO | 91/01156 A1 | 2/1991 |
| WO | 92/16865 A1 | 10/1992 |
| WO | 93/06213 A1 | 4/1993 |
| WO | 93/08829 A1 | 5/1993 |
| WO | 98/38907 A1 | 9/1998 |
| WO | 98/57583 A1 | 12/1998 |
| WO | 00/11511 A1 | 3/2000 |
| WO | 00/44296 A1 | 8/2000 |
| WO | 01/11409 A2 | 2/2001 |
| WO | 03/062802 A2 | 7/2003 |
| WO | 03/073950 A1 | 9/2003 |
| WO | 2004/010856 A1 | 2/2004 |
| WO | 2004/023992 A1 | 3/2004 |
| WO | 2004/096049 A2 | 11/2004 |
| WO | 2005/047813 A1 | 5/2005 |
| WO | 2005/106695 A2 | 11/2005 |
| WO | 2006/029634 A2 | 3/2006 |
| WO | 2006/037132 A1 | 4/2006 |
| WO | 2006/039091 A2 | 4/2006 |
| WO | 2006/061829 A1 | 6/2006 |
| WO | 2006/068875 A2 | 6/2006 |
| WO | 2006/111704 A1 | 10/2006 |
| WO | 2006/119416 A2 | 11/2006 |
| WO | 2006/121851 A2 | 11/2006 |
| WO | 2006/130802 A2 | 12/2006 |
| WO | 2007/002685 A2 | 1/2007 |
| WO | 2007/025230 A2 | 3/2007 |
| WO | 2007/045690 A1 | 4/2007 |
| WO | 2007/058895 A2 | 5/2007 |

(56) References Cited

FOREIGN PATENT DOCUMENTS

| | | | |
|---|---|---|---|
| WO | 2007/067323 A2 | 6/2007 |
| WO | 2007/084995 A2 | 7/2007 |
| WO | 2008/058084 A2 | 5/2008 |
| WO | 2008/069991 A1 | 6/2008 |
| WO | 2008/107905 A2 | 9/2008 |
| WO | 2009/009799 A1 | 1/2009 |
| WO | 2009/009801 A1 | 1/2009 |
| WO | 2009/046431 A1 | 4/2009 |
| WO | 2009/121067 A1 | 10/2009 |
| WO | 2009/137704 A1 | 11/2009 |
| WO | 2011/06886 A2 | 1/2011 |
| WO | 2011/038048 A1 | 3/2011 |
| WO | 2011/081688 A1 | 7/2011 |
| WO | 2012/003369 A2 | 1/2012 |
| WO | 2012/061935 A1 | 5/2012 |
| WO | 2012/061940 A1 | 5/2012 |
| WO | 2012/071388 A2 | 5/2012 |
| WO | 2012/087818 A1 | 6/2012 |
| WO | 2012/098194 A1 | 7/2012 |
| WO | 2012/109676 A1 | 8/2012 |
| WO | 2012/130289 A1 | 10/2012 |
| WO | 2012/154767 A2 | 11/2012 |
| WO | 2012/155040 A1 | 11/2012 |
| WO | 2013/033414 A1 | 3/2013 |
| WO | 2013/033415 A2 | 3/2013 |
| WO | 2013/033418 A1 | 3/2013 |
| WO | 2013/033489 A1 | 3/2013 |
| WO | 2013/033490 A1 | 3/2013 |
| WO | 2013/033592 A1 | 3/2013 |
| WO | 2013/126390 A1 | 8/2013 |
| WO | 2014/109879 A1 | 7/2014 |

OTHER PUBLICATIONS

Sihan et al., 2008, A novel approach to quantitative analysis of intraluminal optical coherence tomography imaging, Comput. Cardiol:1089-1092.
Siwy et al., 2003, Electro-responsive asymmetric nanopores in polyimide with stable ion-current signal, Applied Physics A: Materials Science & Processing 76:781-785.
Smith et al., 1989, Absolute displacement measurements using modulation of the spectrum of white light in a Michelson interferometer, Applied Optics, 28(16):3339-3342.
Smith, 1997, The Scientist and Engineer's Guide to Digital Signal Processing, California Technical Publishing, San Diego, CA:432-436.
Soller, 2003, Polarization diverse optical frequency domain interferometry:All coupler implementation, Bragg Grating, Photosensitivity, and Poling in Glass Waveguides Conference MB4:30-32.
Song et al., 2012, Active tremor cancellation by a "Smart" handheld vitreoretinal microsurgical tool using swept source optical coherence tomography, Optics Express, 20(21):23414-23421.
Stenqvist et al., 1983, Stiffness of central venous catheters, Acta Anaesthesiol Scand., 2:153-157.
Strickland, 1970, Time-Domain Reflectometer Measurements, Tektronix, Beaverton, OR, (107 pages).
Strobl et al., 2009, An Introduction to Recursive Partitioning:Rationale, Application and Characteristics of Classification and Regression Trees, Bagging and Random Forests, Psychol Methods., 14(4):323-348.
Sutcliffe et al., 1986, Dynamics of UV laser ablation of organic polymer surfaces, Journal of Applied Physics, 60(9):3315-3322.
Suzuki, 2013, A novel guidewire approach for handling acute-angle bifurcations, J Inv Cardiol 25(1):48-54.
Tanimoto et al., 2008, A novel approach for quantitative analysis of intracoronary optical coherence tomography: high inter-observer agreement with computer-assisted contour detection, Cathet Cardiovascular Intervent., 72(2):228-235.
Tearney et al., 1997, In vivo Endoscopic Optical Biopsy with Optical Coherence Tomography, Science, 276:2037-2039.
Tonino et al., 2009, Fractional flow reserve versus angiography for guiding percutaneous coronary intervention, The New England Journal of Medicine, 360:213-224.
Toregeani et al., 2008, Evaluation of hemodialysis arteriovenous fistula maturation by color-flow Doppler ultrasound, J Vasc. Bras. 7(3):203-213.
Translation of Notice of Reason(s) for Refusal dated Apr. 30, 2014, for Japanese Patent Application No. 2011-508677, (5 pages).
Translation of Notice of Reason(s) for Refusal dated May 25, 2012, for Japanese Patent Application No. 2009-536425, (3 pages).
Translation of Notice of Reason(s) for Refusal dated Nov. 22, 2012, for Japanese Patent Application No. 2010-516304, (6 pages).
Traunecker et al., 1991, Bispecific single chain molecules (Janusins) target cytotoxic lymphocytes on HIV infected cells, EMBO J., 10:3655-3659.
Trolier-McKinstry et. al., 2004, Thin Film Piezoelectric for MEMS, Journal of Electroceramics 12:7-17.
Tuniz et al., 2010, Weaving the invisible thread: design of an optically invisible metamaterial fibre, Optics Express 18(17):18095-18105.
Turk et al., 1991, Eigenfaces for Recognition, Journal of Cognitive Neuroscience 3(1):71-86.
Tuzel et al., 2006, Region Covariance: A Fast Descriptor for Detection and Classification, European Conference on Computer Vision (ECCV).
Urban et al., 2010, Design of a Pressure Sensor Based on Optical Bragg Grating Lateral Deformation, Sensors (Basel), 10(12):11212-11225.
Vakhtin et al., 2003, Common-path interferometer for frequency-domain optical coherence tomography, Applied Optics, 42(34):6953-6958.
Vakoc et al., 2005, Phase-Resolved Optical Frequency Domain Imaging, Optics Express 13(14):5483-5493.
Verhoeyen et al., 1988, Reshaping human antibodies: grafting an antilysozyme activity, Science, 239:1534-1536.
Villard et al., 2002, Use of a blood substitute to determine instantaneous murine right ventricular thickening with optical coherence tomography, Circulation, 105:1843-1849.
Wang et al., 2002, Optimizing the Beam Patten of a Forward-Viewing Ring-Annular Ultrasound Array for Intravascular Imaging, Transactions on Ultrasonics, Ferroelectrics, and Frequency Control, 49(12).
Wang et al., 2006, Multiple biomarkers for the prediction of first major cardiovascular events and death, The New England Journal of Medicine, 355(25):2631-2639.
Wang et al., 2009, Robust Guidewire Tracking in Fluoroscopy, IEEE Conference on Computer Vision and Pattern Recognition—CVPR 2009:691-698.
Wang et al., 2011, In vivo intracardiac optical coherence tomography imaging through percutaneous access: toward image-guided radio-frequency ablation, J. Biomed. Opt. 0001 16(11):110505-1 (3 pages).
Waterhouse et. al., 1993, Combinatorial infection and in vivo recombination: a strategy for making large phage antibody repertoires, Nucleic Acids Res., 21:2265-2266.
Wegener, 2011, 3D Photonic Metamaterials and Invisibility Cloaks: The Method of Making, MEMS 2011, Cancun, Mexico, Jan. 23-27, 2011.
West et al., 1991, Arterial insufficiency in hemodialysis access procedures: correction by banding technique, Transpl Proc 23(2):1838-40.
Wyawahare et al., 2009, Image registration techniques: an overview, International Journal of Signal Processing, Image Processing and Pattern Recognition, 2(3):11-28.
Yaqoob et al., 2006, Methods and application areas of endoscopic optical coherence tomography, J. Biomed. Opt., 11, 063001-1-063001-19.
Yasuno et al., 2004, Polarization-sensitive complex Fourier domain optical coherence tomography for Jones matrix imaging of biological samples, Applied Physics Letters 85(15):3023-3025.
Zhang et al., 2004, Full range polarization-sensitive Fourier domain optical coherence tomography, Optics Express, 12(24):6033-6039.

(56) References Cited

OTHER PUBLICATIONS

Zitova et al., 2003, Image registration methods: A survey. Image and Vision Computing, 21(11):977-1000.
Abdi et al., 2010, Principal component analysis, Wiley Interdisciplinary Reviews: Computational Statistics 2:433-459.
Adler et al., 2007, Phase-Sensitive Optical Coherence Tomography at up to 370,000 Lines Per Second Using Buffered Fourier Domain Mode-Locked Lasers, Optics Letters, 32(6):626-628.
Agresti, 1996, Models for Matched Pairs, Chapter 8, An Introduction to Categorical Data Analysis, Wiley-Interscience A John Wiley & Sons, Inc., Publication, Hoboken, New Jersey
Akasheh et al., 2004, Development of piezoelectric micromachined ultrasonic transducers, Sensors and Actuators A Physical, 111:275-287.
Amini et al., 1990, Using dynamic programming for solving variational problems in vision, IEEE Transactions on Pattern Analysis and Machine Intelligence, 12(9):855-867.
Bail et al., 1996, Optical coherence tomography with the "Spectral Radar"-Fast optical analysis in volume scatterers by short coherence interferometry, Optics Letters 21(14):1087-1089.
Bain, 2011, Privacy protection and face recognition, Chapter 3, Handbook of Face Recognition, Stan et al., Springer-Verlag.
Barnea et al., 1972, A class of algorithms for fast digital image registration, IEEE Trans. Computers, 21(2):179-186.
Blanchet et al., 1993, Laser Ablation and the Production of Polymer Films, Science, 262(5134):719-721.
Bonnema, 2008, Imaging Tissue Engineered Blood Vessel Mimics with Optical Tomography, College of Optical Sciences dissertation, University of Arizona (252 pages).
Bouma et al., 1999, Power-efficient nonreciprocal interferometer and linear-scanning fiber-optic catheter for optical coherence tomography, Optics Letters, 24(8):531-533.
Breiman, 2001, Random forests, Machine Learning 45:5-32.
Brown, 1992, A survey of image registration techniques, ACM Computing Surveys 24(4):325-376.
Bruining et al., 2009, Intravascular Ultrasound Registration/Integration with Coronary Angiography, Cardiology Clinics, 27(3):531-540.
Brummer, 1997, An euclidean distance measure between covariance matrices of speechcepstra for text-independent speaker recognition, in Proc. South African Symp. Communications and Signal Processing:167-172.
Burr et al., 2005, Searching for the Center of an Ellipse in Proceedings of the 17th Canadian Conference on Computational Geometry:260-263.
Canny, 1986, A computational approach to edge detection, IEEE Trans. Pattern Anal. Mach. Intell. 8:679-698.
Cavalli et al., 2010, Nanosponge formulations as oxygen delivery systems, International Journal of Pharmaceutics 402:254-257.
Choma et al., 2003, Sensitivity Advantage of Swept Source and Fourier Domain Optical Coherence Tomography, Optics Express 11(18):2183-2189.
Clarke et al., 1995, Hypoxia and myocardial ischaemia during peripheral angioplasty, Clinical Radiology, 50(5):301-303.
Collins, 1993, Coronary flow reserve, British Heart Journal 69:279-281.
Communication Mechanisms for Distributed Real-Time Applications, NI Developer Zone, http://zone.ni.eom/devzone/cda/tut/p/id/3105, accessed Jul. 23, 2007.
Cook, 2007, Use and misuse of receiver operating characteristic curve in risk prediction, Circulation 115(7):928-35.
D'Agostino et al., 2001, Validation of the Framingham coronary heart disease prediction score: results of a multiple ethnic group investigation, JAMA 286:180-187.
David et al., 1974, Protein iodination with solid-state lactoperoxidase, Biochemistry 13:1014-1021.
Davies et al., 1985, Plaque fissuring-the cause of acute myocardial infarction, sudden ischaemic death, and crescendo angina, British Heart Journal 53:363-373.
Davies et al., 1993, Risk of thrombosis in human atherosclerotic plaques: role of extracellular lipid, macrophage, and smooth muscle cell content, British Heart Journal 69:377-381.
Deterministic Data Streaming in Distributed Data Acquisition Systems, NI Developer Zone, "What is Developer Zone?", http://zone.ni.eom/devzone/cda/tut/p/id/3105, accessed Jul. 23, 2007.
Eigenwillig, 2008, K-Space Linear Fourier Domain Mode Locked Laser and Applications for Optical Coherence Tomography, Optics Express 16(12):8916-8937.
Elghanian et al., 1997, Selective colorimetric detection of polynucleotides based on the distance-dependent optical properties of gold nanoparticles, Science, 277(5329):1078-1080.
Ergun et al., 2003, Capacitive Micromachined Ultrasonic Transducers:Theory and Technology, Journal of Aerospace Engineering, 16(2):76-84.
Evans et al., 2006, Optical coherence tomography to identify intramucosa carcinoma and high-grade dysplasia in Barrett's esophagus, Clin Gast Hepat 4(1):38-43.
Fatemi et al., 1999, Vibro-acoustography: an imaging modality based on ultrasound-stimulated acoustic emission, PNAS U.S.A., 96(12):6603-6608.
Felzenszwalb et al., 2005, Pictorial Structures for Object Recognition, International Journal of Computer Vision, 61(1):55-79.
Ferring et al., 2008, Vasculature ultrasound for the pre-operative evaluation prior to arteriovenous fistula formation for haemodialysis: review of the evidence, Nephrol. Dial. Transplant. 23(6):1809-1815.
Fischler et al., 1973, The representation and matching of pictorial structures, IEEE Transactions on Computer 22:67-92.
Fleming et al., 2010, Real-time monitoring of cardiac radio-frequency ablation lesion formation using an optical coherence tomography forward-imaging catheter, Journal of Biomedical Optics 15 (3):030516-1 (3 pages).
Fookes et al., 2002, Rigid and non-rigid image registration and its association with mutual information:A review, Technical Report ISBN:1 86435 569 7, RCCVA, QUT.
Forstner & Moonen, 1999, A metric for covariance matrices, In Technical Report of the Dpt of Geodesy and Geoinformatics, Stuttgart University, 113-128.
Goel et al., 2006, Minimally Invasive Limited Ligation Endoluminal-assisted Revision (MILLER) for treatment of dialysis access-associated steal syndrome, Kidney Int 70(4):765-70.
Gotzinger et al., 2005, High speed spectral domain polarization sensitive optical coherence tomography of the human retina, Optics Express 13(25):10217-10229.
Gould et al., 1974, Physiologic basis for assessing critical coronary stenosis, American Journal of Cardiology, 33:87-94.
Griffiths et al., 1993, Human anti-self antibodies with high specificity from phage display libraries, The EMBO Journal, 12:725-734.
Griffiths et al., 1994, Isolation of high affinity human antibodies directly from large synthetic repertoires, The EMBO Journal, 13(14):3245-3260.
Grund et al., 2010, Analysis of biomarker data:logs, odds, ratios and ROC curves, Curr Opin HIV AIDS 5(6):473-479.
Harrison et al., 2011, Guidewire Stiffness: What's in a name?, J Endovasc Ther, 18(6):797-801.
Huber et al., 2005, Amplified, Frequency Swept Lasers for Frequency Domain Reflectometry and OCT Imaging: Design and Scaling Principles, Optics Express 13(9):3513-3528.
Huber et al., 2006, Fourier Domain Mode Locking (FDML): A New Laser Operating Regime and Applications for Optical Coherence Tomography, Optics Express 14(8):3225-3237.
International Search Report and Written Opinion dated Mar. 11, 2014, for International Patent Application No. PCT/US13/75675, filed Dec. 17, 2013 (7 pages).
International Search Report and Written Opinion dated Mar. 19, 2014, for International Patent Application No. PCT/US13/075353, filed Dec. 16, 2013 (8 pages).
Little et al., 1991, The underlying coronary lesion in myocardial infarction:implications for coronary angiography, Clinical Cardiology, 14(11):868-874.

(56) References Cited

OTHER PUBLICATIONS

Loo, 2004, Nanoshell Enabled Photonics-Based Imaging and Therapy of Cancer, Technology in Cancer Research & Treatment 3(1):33-40.
Machine translation of JP 2000-097846.
Machine translation of JP 2000-321034.
Machine translation of JP 2000-329534.
Machine translation of JP 2004-004080.
Maintz et al., 1998, An Overview of Medical Image Registration Methods, Technical Report UU-CS, (22 pages).
Mamas et al., 2010, Resting Pd/Pa measured with intracoronary pressure wire strongly predicts fractional flow reserve, Journal of Invasive Cardiology 22(6):260-265.
Marks et al., 1991, By-passing Immunization Human Antibodies from V-gene Libraries Displayed on Phage, J. Mol. Biol. 222:581-597.
Marks et al., 1992, By-Passing Immunization:Building High Affinity Human Antibodies by Chain Shuffling, BioTechnol., 10:779-783.
Maruno et al., 1991, Fluorine containing optical adhesives for optical communications systems, J. Appl. Polymer. Sci. 42:2141-2148.
McCafferty et al., 1990, Phage antibodies: filamentous phage displaying antibody variable domains, Nature 348:552-554.
Mendieta et al., 1996, Complementary sequence correlations with applications to reflectometry studies, Instrumentation and Development 3(6):37-46.
Mickley, 2008, Steal Syndrome-strategies to preserve vascular access and extremity, Nephrol Dial Transplant 23:19-24.
Miller et al., 2010, The Miller banding procedure is an effective method for treating dialysis-associated steal syndrome, Kidney International 77:359-366.
Milstein et al., 1983, Hybrid hybridomas and their use in immunohistochemistry, Nature 305:537-540.
Mindlin et al., 1936, A force at a point of a semi-infinite solid, Physics, 7:195-202.
Morrison et al., 1984, Chimeric human antibody molecules: mouse antigen-binding domains with human constant region domains, PNAS 81:6851-6855.
Munson et al., 1980, Ligand: a versatile computerized approach for characterization of ligand-binding systems, Analytical Biochemistry, 107:220-239.
Nezarn, 2008, High Speed Polygon-Scanner-Based Wavelength-Swept Laser Source in the Telescope-Less Configurations with Application in Optical Coherence Tomography, Optics Letters 33(15):1741-1743.
Nissen, 2001, Coronary Angiography and Intravascular Ultrasound, American Journal of Cardiology, 87 (suppl):15A-20A.
Nitenberg et al., 1995, Coronary vascular reserve in humans: a critical review of methods of evaluation and of interpretation of the results, Eur Heart J. 16(Suppl 1):7-21.
Notice of Reason(s) for Refusal dated Apr. 30, 2013, for Japanese Patent Application No. 2011-508677 for Optical Imaging Catheter for Aberation Balancing to Volcano Corporation, which application is a Japanese national stage entry of PCT/US2009/043181 with international filing date May 7, 2009, of the same title, published on Nov. 12, 2009, as WO 2009/137704, and accompanying English translation of the Notice of Reason(s) for Refusal and machine translations of JP11-56786 and JP2004-290548 (56 pages).
Nygren, 1982, Conjugation of horseradish peroxidase to Fab fragments with different homobifunctional and heterobifunctional cross-linking reagents. A comparative study, J. Histochem. and Cytochem. 30:407-412.
Oesterle et al., 1986, Angioplasty at coronary bifurcations: single-guide, two-wire technique, Cathet Cardiovasc Diagn., 12:57-63.
Okuno et al., 2003, Recent Advances in Optical Switches Using Silica-based PLC Technology, NTT Technical Review 1(7):20-30.
Oldenburg et al., 1998, Nanoengineering of Optical Resonances, Chemical Physics Letters 288:243-247.
Oldenburg et al., 2003, Fast-Fourier-Domain Delay Line for in Vivo Optical Coherence Tomography with a Polygonal Scanner, Applied Optics, 42(22):4606-4611.
Othonos, 1997, Fiber Bragg gratings, Review of Scientific Instruments 68(12):4309-4341.
Owens et al., 2007, A Survey of General-Purpose Computation on Graphics Hardware, Computer Graphics Forum 26(1):80-113.
Pain et al., 1981, Preparation of protein A-peroxidase mono conjugate using a heterobifunctional reagent, and its use in enzyme immunoassays, J Immunol Methods, 40:219-30.
Park et al., 2005, Real-time fiber-based multi-functional spectral-domain optical coherence tomography at 1.3 um., Optics Express 13(11):3931-3944.
Pasquesi et al., 2006, In vivo detection of exercise induced ultrastructural changes in genetically-altered murine skeletal muscle using polarization-sensitive optical coherence tomography, Optics Express 14(4)1547-1556.
Pepe et al., 2004, Limitations of the odds ratio in gauging the performance of a diagnostic, prognostic, or screening marker, American Journal of Epidemiology 159(9):882-890.
Persson et al., 1985, Acoustic impedance matching of medical ultrasound transducers, Ultrasonics, 23(2):83-89.
Placht et al., 2012, Fast time-of-flight camera based surface registration for radiotherapy patient positioning, Medical Physics 39(1):4-17.
Rabbani et al., 1999, Review: Strategies to achieve coronary arterial plaque stabilization, Cardiovascular Research 41:402-417.
Radvany et al., 2008, Plaque Excision in Management of Lower Extremity Peripheral Arterial Disease with the SilverHawk Atherectomy Catheter, Seminars in Interventional Radiology, 25(1):11-19.
Reddy et al., 1996, An FFT-Based Technique for Translation, Rotation, and Scale-Invariant Image Registration, IEEE Transaction on Image Processing 5(8):1266-1271.
Riechmann et al., 1988, Reshaping human antibodies for therapy, Nature, 332:323-327.
Rivers et al., 1992, Correction of steal syndrome secondary to hemodialysis access fistulas: a simplified quantitative technique, Surgery, 112(3):593-7.
Robbin et al., 2002, Hemodialysis Arteriovenous Fistula Maturity: US Evaluation, Radiology 225:59-64.
Rollins et al., 1998, In vivo video rate optical coherence tomography, Optics Express 3:219-229.
Sarunic et al., 2005, Instantaneous Complex Conjugate Resolved Spectral Domain and Swept-Source OCT Using 3×3 Fiber Couplers, Optics Express 13(3):957-967.
Satiani et al., 2009, Predicted Shortage of Vascular Surgeons in the United States, J. Vascular Surgery 50:946-952.
Schneider et al., 2006, T-banding: A technique for flow reduction of a hyper-functioning arteriovenous fistula, J Vasc Surg. 43(2):402-405.
Sen et al., 2012, Development and validation of a new adenosine-independent index of stenosis severity from coronary wave-intensity analysis, Journal of the American College of Cardiology 59(15):1392-1402.
Setta et al., 2005, Soft versus firm embryo transfer catheters for assisted reproduction: a systematic review and meta-analysis, Human Reproduction, 20(11):3114-3121.
Seward et al., 1996, Ultrasound Cardioscopy: Embarking on New Journey, Mayo Clinic Proceedings 71(7):629-635.
Shen et al., 2006, Eigengene-based linear discriminant model for tumor classification using gene expression microarray data, Bioinformatics 22(21):2635-2642.
International Search Report and Written Opinion dated Nov. 2, 2012, for International Patent Application No. PCT/US12/53168, filed Aug. 30, 2013 (8 pages).
International Search Report and Written Opinion dated Apr. 14, 2014, for International Patent Application No. PCT/US2013/076148, filed Dec. 18, 2013 (8 pages).
International Search Report and Written Opinion dated Apr. 21, 2014, for International Patent Application No. PCT/US2013/076015, filed Dec. 18, 2013 (7 pages).

(56) References Cited

OTHER PUBLICATIONS

International Search Report and Written Opinion dated Apr. 23, 2014, for International Patent Application No. PCT/US2013/075328, filed Dec. 16, 2013 (8 pages).
International Search Report and Written Opinion dated Apr. 29, 2014, for International Patent Application No. PCT/US13/76093, filed Dec. 18, 2013 (6 pages).
International Search Report and Written Opinion dated Apr. 9, 2014, for International Patent Application No. PCT/US13/75089, filed Dec. 13, 2013 (7 pages).
International Search Report and Written Opinion dated Feb. 21, 2014, for International Patent Application No. PCT/US13/76053, filed Dec. 18, 2013 (9 pages).
International Search Report and Written Opinion dated Feb. 21, 2014, for International Patent Application No. PCT/US2013/076965, filed Dec. 20, 2013 (6 pages).
International Search Report and Written Opinion dated Feb. 27, 2014, for International Patent Application No. PCT/US13/75416, filed Dec. 16, 2013 (7 pages).
International Search Report and Written Opinion dated Feb. 28, 2014, for International Patent Application No. PCT/US13/75653, filed Dec. 17, 2013 (7 pages).
International Search Report and Written Opinion dated Feb. 28, 2014, for International Patent Application No. PCT/US13/75990, filed Dec. 18, 2013 (7 pages).
International Search Report and Written Opinion dated Jan. 16, 2009, for International Patent Application No. PCT/US08/78963 filed Oct. 6, 2008 (7 pages).
International Search Report and Written Opinion dated Jul. 30, 2014, for International Patent Application No. PCT/US14/21659, filed Mar. 7, 2014 (15 pages).
International Search Report and Written Opinion dated Mar. 10, 2014, for International Patent Application No. PCT/US2013/076212, filed Dec. 18, 2013 (8 pages).
International Search Report and Written Opinion dated Mar. 11, 2014, for International Patent Application No. PCT/US13/76173, filed Dec. 16, 2013 (9 pages).
International Search Report and Written Opinion dated Mar. 11, 2014, for International Patent Application No. PCT/US13/76449, filed Dec. 19, 2013 (9 pages).
International Search Report and Written Opinion dated Mar. 18, 2014, for International Patent Application No. PCT/US2013/076502, filed Dec. 19, 2013 (7 pages).
International Search Report and Written Opinion dated Mar. 18, 2014, for International Patent Application No. PCT/US2013/076788, filed Dec. 20, 2013 (7 pages).
International Search Report and Written Opinion dated Mar. 19, 2014, for International Patent Application No. PCT/US13/75349, filed Dec. 16, 2013 (10 pages).
International Search Report and Written Opinion dated Mar. 19, 2014, for International Patent Application No. PCT/US2013/076587, filed Dec. 19, 2013 (10 pages).
International Search Report and Written Opinion dated Mar. 19, 2014, for International Patent Application No. PCT/US2013/076909, filed Dec. 20, 2013 (7 pages).
International Search Report and Written Opinion dated Mar. 7, 2014, for International Patent Application No. PCT/US2013/076304, filed Dec. 18, 2013 (9 pages).
International Search Report and Written Opinion dated Mar. 7, 2014, for International Patent Application No. PCT/US2013/076480, filed Dec. 19, 2013 (8 pages).
International Search Report and Written Opinion dated Mar. 7, 2014, for International Patent Application No. PCT/US2013/076512, filed Dec. 19, 2013 (8 pages).
International Search Report and Written Opinion dated Mar. 7, 2014, for International Patent Application No. PCT/US2013/076531, filed Dec. 19, 2013 (10 pages).

Jakobovits et al., 1993, Analysis of homozygous mutant chimeric mice:deletion of the immunoglobulin heavy-chain joining region blocks B-cell development and antibody production, PNAS USA 90:2551-255.
Jakobovits et al., 1993, Germ-line transmission and expression of a human-derived yeast artificial chromosome, Nature 362:255-258.
Jang et al., 2002, Visualization of Coronary Atherosclerotic Plaques in Patients Using Optical Coherence Tomography: Comparison With Intravascular Ultrasound, Journal of the American College of Cardiology 39:604-609.
Jiang et al. 1992, Image registration of multimodality 3-D medical images by chamfer matching, Proc. SPIE 1660, Biomedical Image Processing and Three-Dimensional Microscopy, 356-366.
Johnson et al., 1993, Human antibody engineering: Current Opinion in Structural Biology, 3:564-571.
Jones et al., 1986, Replacing the complementarity-determining regions in a human antibody with those from a mouse, Nature, 321:522-525.
Juviler et al., 2008, Anorectal sepsis and fistula-in-ano, Surgical Technology International, 17:139-149.
Karapatis et al., 1998, Direct rapid tooling:a review of current research, Rapid Prototyping Journal, 4(2):77-89.
Karp et al., 2009, The benefit of time-of-flight in PET imaging, J Nucl Med 49:462-470.
Kelly et al., 2005, Detection of Vascular Adhesion Molecule-1 Expression Using a Novel Multimodal Nanoparticle, Circulation Research 96:327-336.
Kemp et al., 2005, Depth Resolved Optic Axis Orientation in Multiple Layered Anisotropic Tissues Measured with Enhanced Polarization Sensitive Optical Coherence Tomography, Optics Express 13(12):4507-4518.
Kersey et al., 1991, Polarization insensitive fiber optic Michelson interferometer, Electron. Lett. 27:518-520.
Kheir et al., 2012, Oxygen Gas-Filled Microparticles Provide Intravenous Oxygen Delivery, Science Translational Medicine 4(140):140ra88 (10 pages).
Khuri-Yakub et al., 2011, Capacitive micromachined ultrasonic transducers for medical imaging and therapy, J Micromech Microeng. 21(5):054004-054014.
Kirkman, 1991, Technique for flow reduction in dialysis access fistulas, Surg Gyn Obstet, 172(3):231-3.
Kohler et al., 1975, Continuous cultures of fused cells secreting antibody of predefined specificity, Nature, 256:495-7.
Koo et al., 2011, Diagnosis of IschemiaCausing Coronary Stenoses by Noninvasive Fractional Flow Reserve Computed From Coronary Computed Tomographic Angiograms, J Am Coll Cardiol 58(19):1989-1997.
Kozbor et al., 1984, A human hybrid myeloma for production of human monoclonal antibodies, J. Immunol., 133:3001-3005.
Kruth et al., 2003, Lasers and materials in selective laser sintering, Assembly Automation, 23(4):357-371.
Kumagai et al., 1994, Ablation of polymer films by a femtosecond high-peak-power Ti:sapphire laser at 798 nm, Applied Physics Letters, 65(14):1850-1852.
Larin et al., 2002, Noninvasive Blood Glucose Monitoring with Optical Coherence Tomography: a pilot study in human subjects, Diabetes Care, 25(12):2263-7.
Larin et al., 2004, Measurement of Refractive Index Variation of Physiological Analytes using Differential Phase OCT, Proc of SPIE 5325:31-34.
Laufer, 1996, Introduction to Optics and Lasers in Engineering, Cambridge University Press, Cambridge UK:156-162.
Lefevre et al., 2001, Stenting of bifurcation lesions:a rational approach, J. Interv. Cardiol., 14(6):573-585.
Li et al., 2000, Optical Coherence Tomography: Advanced Technology for the Endoscopic Imaging of Barrett's Esophagus, Endoscopy, 32(12):921-930.

\* cited by examiner

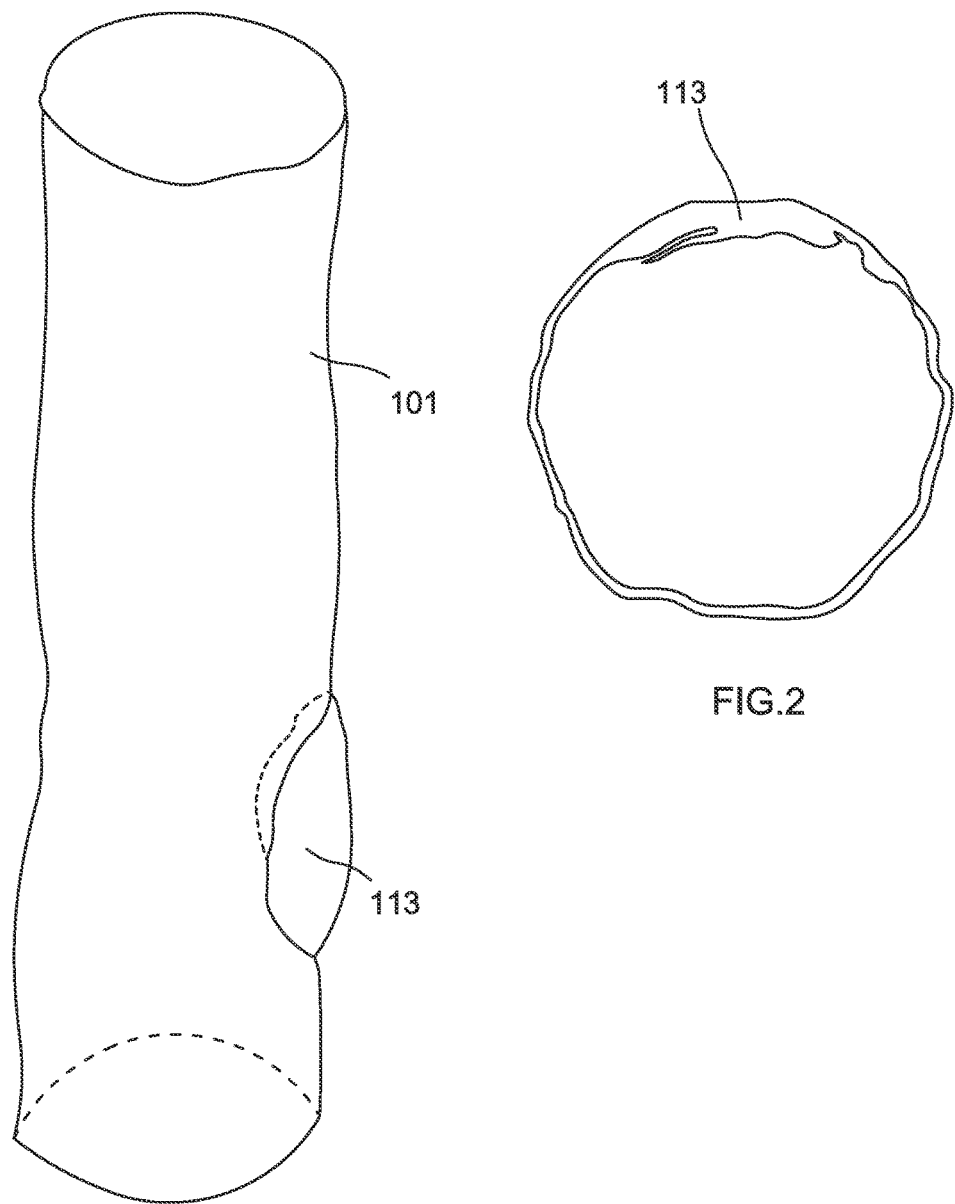

GUIDEWIRE ARTIFACT REMOVAL IN IMAGES

RELATED APPLICATION

This application claims the benefit of and priority to U.S. Provisional No. 61/710,437, filed Oct. 5, 2012, which is incorporated by reference in its entirety.

TECHNICAL FIELD

The invention relates generally to the removal of guidewire artifacts in rotational medical imaging techniques.

BACKGROUND

Tomographic imaging systems allow for high-resolution cross-sectional imaging in biological systems, and include, for example, optical coherence tomography systems, ultrasound imaging systems, and computed tomography systems. Tomographic imaging catheters allow for imaging of the subsurface of a lumen or vessel within the body, such as a blood vessel, through a minimally invasive procedure.

Typical tomographic imaging catheters consist of an imaging core, such as optical or ultrasound probes, disposed within a catheter that rotates and moves longitudinally through a lumen, while recording an image video loop of the lumen. The motion results in a 3D dataset, where each frame provides a 360 degree slice of the vessel at different longitudinal sections.

Prior to insertion of the imaging catheter to the target imaging area, a guidewire is directed into the lumen and retained at the target imaging area. The guidewire is typically a thin, flexible wire that is inserted into a lumen to act as a guide for subsequent insertion of the imaging catheter to the target imaging area. Once at the target imaging area, the imaging catheter rotates while moving longitudinally alongside the guidewire to acquire imaging data.

Because the imaging core rotationally sweeps past the guidewire during each rotation, the resulting images typically include a guidewire shadow or artifact that obscures imaging of tissue located behind the guidewire. The guidewire artifact is caused by the inability of the sensing energy, such as light or sound, to adequately penetrate the guidewire. The guidewire artifact is considered to be an unavoidable discontinuity in the imaging data that reduces image quality and can lead to misinterpretation of the resulting medical images.

SUMMARY

This invention generally improves image quality of tomographic imaging systems that use a rotating imaging probe in parallel with an object, such as a guidewire, that creates a discontinuity in an imaging data set. Through use of the image processing techniques, discontinuities, such as guidewire artifacts, are removed from an imaging data set, and thus removed from any resulting images. The resulting images with the artifacts removed include B-scans or scan-converted images. This advantageously reduces any error associated with misinterpretation of the guidewire artifact in the resulting images and overall improves image quality.

Guidewire artifacts and other artifacts can be removed from images acquired from any tomographic imaging system that utilizes a rotating probe, including, for example, optical coherence tomography, ultrasound technology, intravascular spectroscopy, or photo-acoustic tomography. The medical images acquired with rotating probes are typically intraluminal images taken within a biological lumen, such as a blood vessel and an intestine.

In certain aspects, a guidewire artifact is removed by acquiring at least two images an imaging surface in which image is formed from a set of imaging data. The imaging surface can include tissue, stents, plaque, ect. The guidewire artifact present in one of the at least two images is detected, and then replaced with data representing the imaging surface obtained from at least one other image.

In some embodiments, the at least two images of the imaging surface are acquired by repeated imaging of the same imaging surface. For catheter imaging, the images are acquired by pulling back or pushing forward the imaging catheter across the same region of the imaging surface within a lumen. During image acquisition, the guidewire is rotated or moved to a different position within the lumen so that the at least two images are of the same imaging surface with the guidewire in a different location.

The guidewire artifact is then detected in at least one of the images. The guidewire artifact can be automatically or manually detected in an image. After the guidewire artifact is detected within one of the at least two images, the guidewire artifact is replaced with data representing the imaging surface at the same location obtained from another one of the at least two images.

In certain embodiments, prior to detection of the guidewire artifact, the acquired images are registered to obtain the Cartesian coordinates for the imaging data set of each image. Registration allows for data from each image to be compared and integrated. The images can be manually or automatically registered using, for example, a phase correlation technique. By detecting the guidewire artifact, the position and the size of the guidewire within the Cartesian coordinate system is determined. Because the guidewire is moved during imaging, the guidewire artifact present in one of the images shares the same Cartesian coordinates as the imaging surface obtained from another image of the at least two images. Data representing the detected guidewire artifact is then replaced with data representing the imaging surface sharing the same Cartesian coordinates with the guidewire from another one of the at least two images. In one aspect, the resulting image with the guidewire artifact removed is interpolated to improve image quality.

Other and further aspects and features of the invention will be evident from the following detailed description and accompanying drawings, which are intended to illustrate, not limit, the invention.

BRIEF DESCRIPTION OF DRAWINGS

FIG. 1 is a perspective view of a vessel.

FIG. 2 is a cross sectional view of the vessel shown in FIG. 1.

DESCRIPTION

Figure 3:
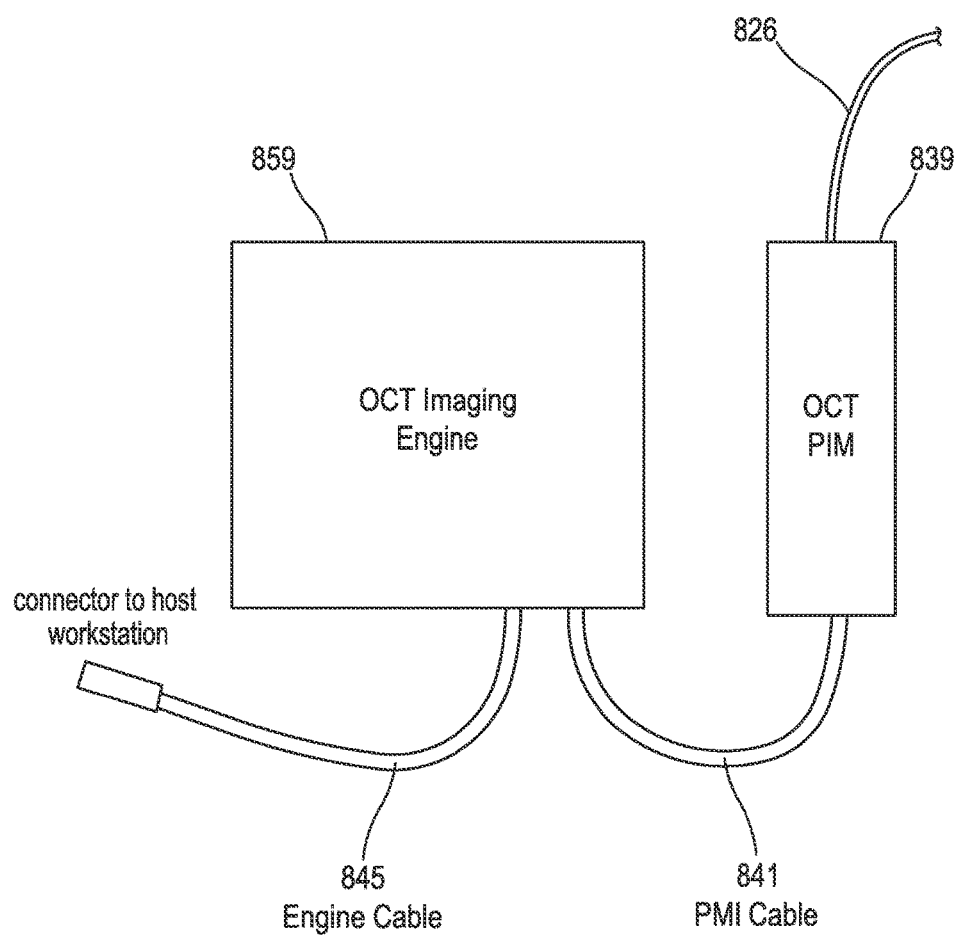
FIG. 3 is a diagram of components of an optical coherence tomography (OCT) system.

This invention generally relates to the removal of guidewire artifacts in medical images obtained from tomographic imaging systems that use a rotational imaging probe in parallel with a guidewire. As the imaging probe rotates to obtain an image, the guidewire often appears as an artifact within the image data set and resulting images. Through use of image processing techniques, artifacts are removed from the imaging data set in order to improve image quality and interpretability.

In certain aspects, in order to remove a guidewire artifact or other shadowing from an image, at least two images are taken of an imaging surface having the guidewire or other shadow causing obstruction moved or rotated to a different location. The resulting images are of the same imaging surface region having the resulting guidewire artifact or shadow in a different location. The guidewire artifact or shadow within one of the images is then replaced with data representing the imaging surface at the same location from one of the other images. This substitution removes the guidewire artifact from the image and provides a true substitution of the data representing the imaging surface lost to the shadow.

Accordingly, although aspects of the invention are generally applicable to rotational imaging systems, this invention is also contemplated for use in any medical imaging system that has a constant artifact or shadow within the imaging region that can be relocated, so that in image post-processing the artifact within one image can be replaced with data representing the imaging surface from another image. Such medical imaging systems include, for example, optical coherence tomography systems, intravascular ultrasound ("IVUS") systems, spectroscopy, photoacoustic tomography systems, combined ultrasound and OCT systems, RAMAN, alternative interferometric techniques, computed tomography, and any other tomographic imaging technique. Although the exemplifications described herein are drawn to the invention as applied to an OCT system, at least all of these techniques are contemplated for use with the systems and methods of the present invention.

Systems and methods of the invention have application in intravascular imaging methodologies such as intravascular ultrasound (IVUS) and optical coherence tomography (OCT) among others that produce a three-dimensional image of a lumen. A segment of a lumen 101 is shown in FIG. 1 having a feature 113 of interest. FIG. 2 shows a cross-section of lumen 101 through feature 113. In certain embodiments, intravascular imaging involves positioning an imaging device near feature 113 and collecting data representing a three-dimensional image.

OCT is a medical imaging methodology using a specially designed catheter with a miniaturized near infrared light-emitting probe attached to the distal end of the catheter. As an optical signal acquisition and processing method, it captures micrometer-resolution, three-dimensional images from within optical scattering media (e.g., biological tissue). Commercially available OCT systems are employed in diverse applications, including art conservation and diagnostic medicine, notably in ophthalmology where it can be used to obtain detailed images from within the retina. The detailed images of the retina allow one to identify several eye diseases and eye trauma. Recently it has also begun to be used in interventional cardiology to help diagnose coronary artery disease. OCT allows the application of interferometric technology to see from inside, for example, blood vessels, visualizing the endothelium (inner wall) of blood vessels in living individuals.

Other applications of OCT and other signal processing imaging systems for biomedical imaging include use in: dermatology in order to image subsurface structural and blood flow formation; dentistry in order to image the structure of teeth and gum line to identify and track de-mineralization and re-mineralization, tarter, caries, and periodontal disease; gastroenterology in order to image the gastrointestinal tract to detect polyps and inflammation, such as that caused by Crohn's disease and ulcerative colitis; cancer diagnostics in order to discriminate between malignant and normal tissue.

Generally, an OCT system comprises three components which are 1) an imaging catheter 2) OCT imaging hardware, 3) host application software. When utilized, the components are capable of obtaining OCT data, processing OCT data, and transmitting captured data to a host system. OCT systems and methods are generally described in Castella et al., U.S. Pat. No. 8,108,030, Milner et al., U.S. Patent Application Publication No. 2011/0152771, Condit et al., U.S. Patent Application Publication No. 2010/0220334, Castella et al., U.S. Patent Application Publication No. 2009/0043191, Milner et al., U.S. Patent Application Publication No. 2008/0291463, and Kemp, N., U.S. Patent Application Publication No. 2008/0180683, the content of each of which is incorporated by reference in its entirety. In certain embodiments, systems and methods of the invention include processing hardware configured to interact with more than one different three dimensional imaging system so that the tissue imaging devices and methods described here in can be alternatively used with OCT, IVUS, or other hardware.

Various lumen of biological structures may be imaged with aforementioned imaging technologies in addition to blood vessels, including, but not limited, to vasculature of the lymphatic and nervous systems, various structures of the gastrointestinal tract including lumen of the small intestine, large intestine, stomach, esophagus, colon, pancreatic duct, bile duct, hepatic duct, lumen of the reproductive tract including the vas deferens, vagina, uterus and fallopian tubes, structures of the urinary tract including urinary collecting ducts, renal tubules, ureter, and bladder, and structures of the head and neck and pulmonary system including sinuses, parotid, trachea, bronchi, and lungs.

The arteries of the heart are particularly useful to examine with imaging devices such as OCT. OCT imaging of the coronary arteries can determine the amount of plaque built up at any particular point in the coronary artery. The accumulation of plaque within the artery wall over decades is the setup for vulnerable plaque which, in turn, leads to heart attack and stenosis (narrowing) of the artery. OCT is useful in determining both plaque volume within the wall of the artery and/or the degree of stenosis of the artery lumen. It can be especially useful in situations in which angiographic imaging is considered unreliable, such as for the lumen of ostial lesions or where angiographic images do not visualize lumen segments adequately. Example regions include those with multiple overlapping arterial segments. It is also used to assess the effects of treatments of stenosis such as with hydraulic angioplasty expansion of the artery, with or without stents, and the results of medical therapy over time. In an exemplary embodiment, the invention provides a system for capturing a three dimensional image by OCT.

In OCT, a light source delivers a beam of light to an imaging device to image target tissue. Light sources can include pulsating light sources or lasers, continuous wave light sources or lasers, tunable lasers, broadband light source, or multiple tunable laser. Within the light source is an optical amplifier and a tunable filter that allows a user to select a wavelength of light to be amplified. Wavelengths commonly used in medical applications include near-infrared light, for example between about 800 nm and about 1700 nm.

Apsects of the invention apply to imaging data obtained from obtained from any OCT system, including OCT systems that operate in either the time domain or frequency (high definition) domain. Basic differences between time-domain OCT and frequency-domain OCT is that in time-domain OCT, the scanning mechanism is a movable mirror, which is scanned as a function of time during the image acquisition. However, in the frequency-domain OCT, there are no moving parts and the image is scanned as a function of frequency or wavelength.

In time-domain OCT systems an interference spectrum is obtained by moving the scanning mechanism, such as a reference mirror, longitudinally to change the reference path and match multiple optical paths due to reflections within the sample. The signal giving the reflectivity is sampled over time, and light traveling at a specific distance creates interference in the detector. Moving the scanning mechanism laterally (or rotationally) across the sample produces two-dimensional and three-dimensional images.

In frequency domain OCT, a light source capable of emitting a range of optical frequencies excites an interferometer, the interferometer combines the light returned from a sample with a reference beam of light from the same source, and the intensity of the combined light is recorded as a function of optical frequency to form an interference spectrum. A Fourier transform of the interference spectrum provides the reflectance distribution along the depth within the sample.

Several methods of frequency domain OCT are described in the literature. In spectral-domain OCT (SD-OCT), also sometimes called "Spectral Radar" (Optics letters, Vol. 21, No. 14 (1996) 1087-1089), a grating or prism or other means is used to disperse the output of the interferometer into its optical frequency components. The intensities of these separated components are measured using an array of optical detectors, each detector receiving an optical frequency or a fractional range of optical frequencies. The set of measurements from these optical detectors forms an interference spectrum (Smith, L. M. and C. C. Dobson, Applied Optics 28: 3339-3342), wherein the distance to a scatterer is determined by the wavelength dependent fringe spacing within the power spectrum. SD-OCT has enabled the determination of distance and scattering intensity of multiple scatters lying along the illumination axis by analyzing a single the exposure of an array of optical detectors so that no scanning in depth is necessary. Typically the light source emits a broad range of optical frequencies simultaneously.

Alternatively, in swept-source OCT, the interference spectrum is recorded by using a source with adjustable optical frequency, with the optical frequency of the source swept through a range of optical frequencies, and recording the interfered light intensity as a function of time during the sweep. An example of swept-source OCT is described in U.S. Pat. No. 5,321,501.

Generally, time domain systems and frequency domain systems can further vary in type based upon the optical layout of the systems: common beam path systems and differential beam path systems. A common beam path system sends all produced light through a single optical fiber to generate a reference signal and a sample signal whereas a differential beam path system splits the produced light such that a portion of the light is directed to the sample and the other portion is directed to a reference surface. Common beam path systems are described in U.S. Pat. No. 7,999,938; U.S. Pat. No. 7,995,210; and U.S. Pat. No. 7,787,127 and differential beam path systems are described in U.S. Pat. No. 7,783,337; U.S. Pat. No. 6,134,003; and U.S. Pat. No. 6,421,164, the contents of each of which are incorporated by reference herein in its entirety.

In certain embodiments, the invention provides a differential beam path OCT system with intravascular imaging capability as illustrated in FIG. 3. For intravascular imaging, a light beam is delivered to the vessel lumen via a fiber-optic based imaging catheter 826. The imaging catheter is connected through hardware to software on a host workstation. The hardware includes an imagining engine 859 and a handheld patient interface module (PIM) 839 that includes user controls. The proximal end of the imaging catheter is connected to PIM 839, which is connected to an imaging engine as shown in FIG. 3.

Figure 4:
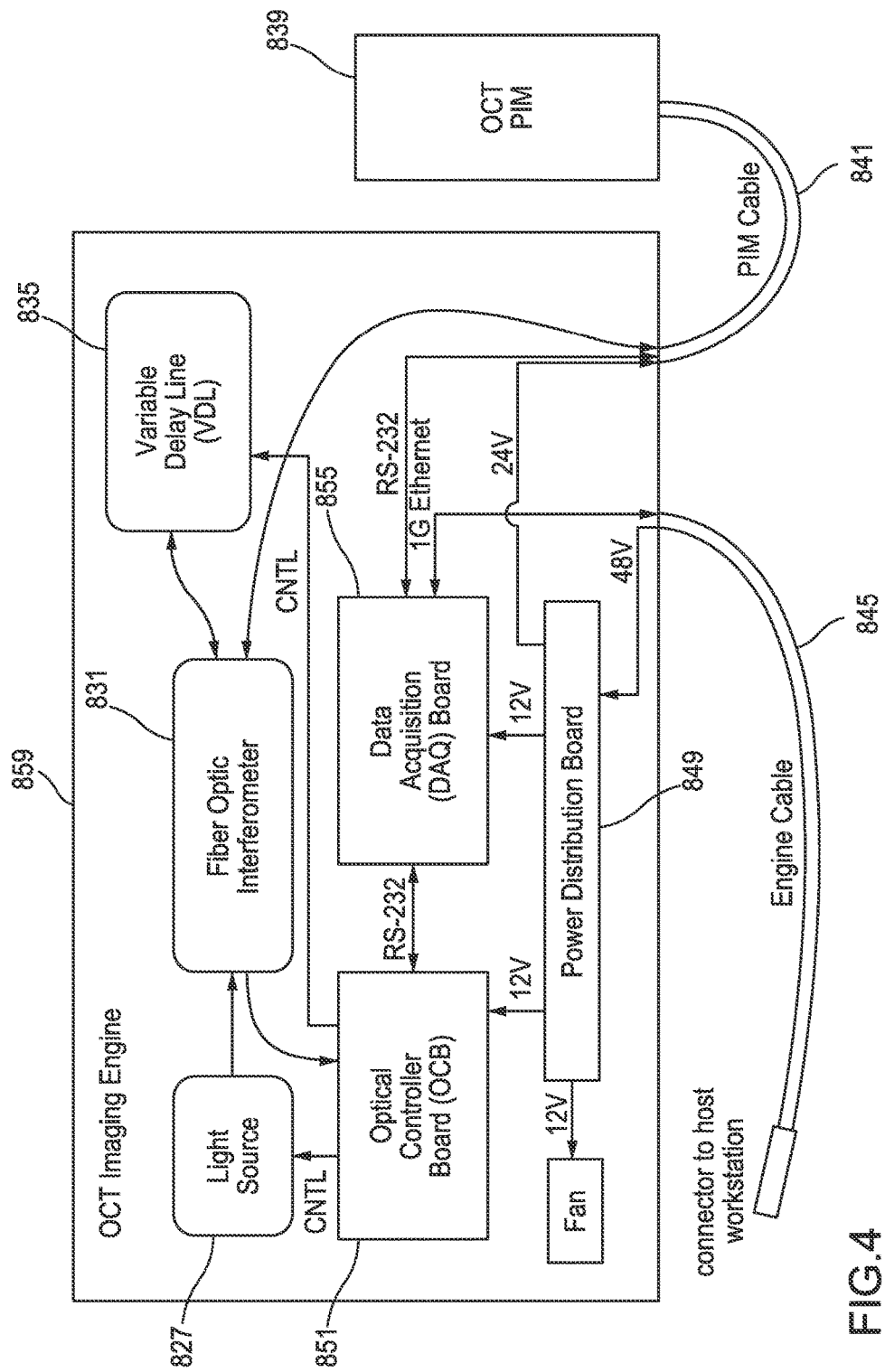
FIG. 4 is a diagram of the imaging engine shown in FIG. 3.

As shown in FIG. 4, the imaging engine 859 (e.g., a bedside unit) houses a power supply 849, light source 827, interferometer 831, and variable delay line 835 as well as a data acquisition (DAQ) board 855 and optical controller board (OCB) 851. A PIM cable 841 connects the imagine engine 859 to the PIM 839 and an engine cable 845 connects the imaging engine 859 to the host workstation.

Figure 5:
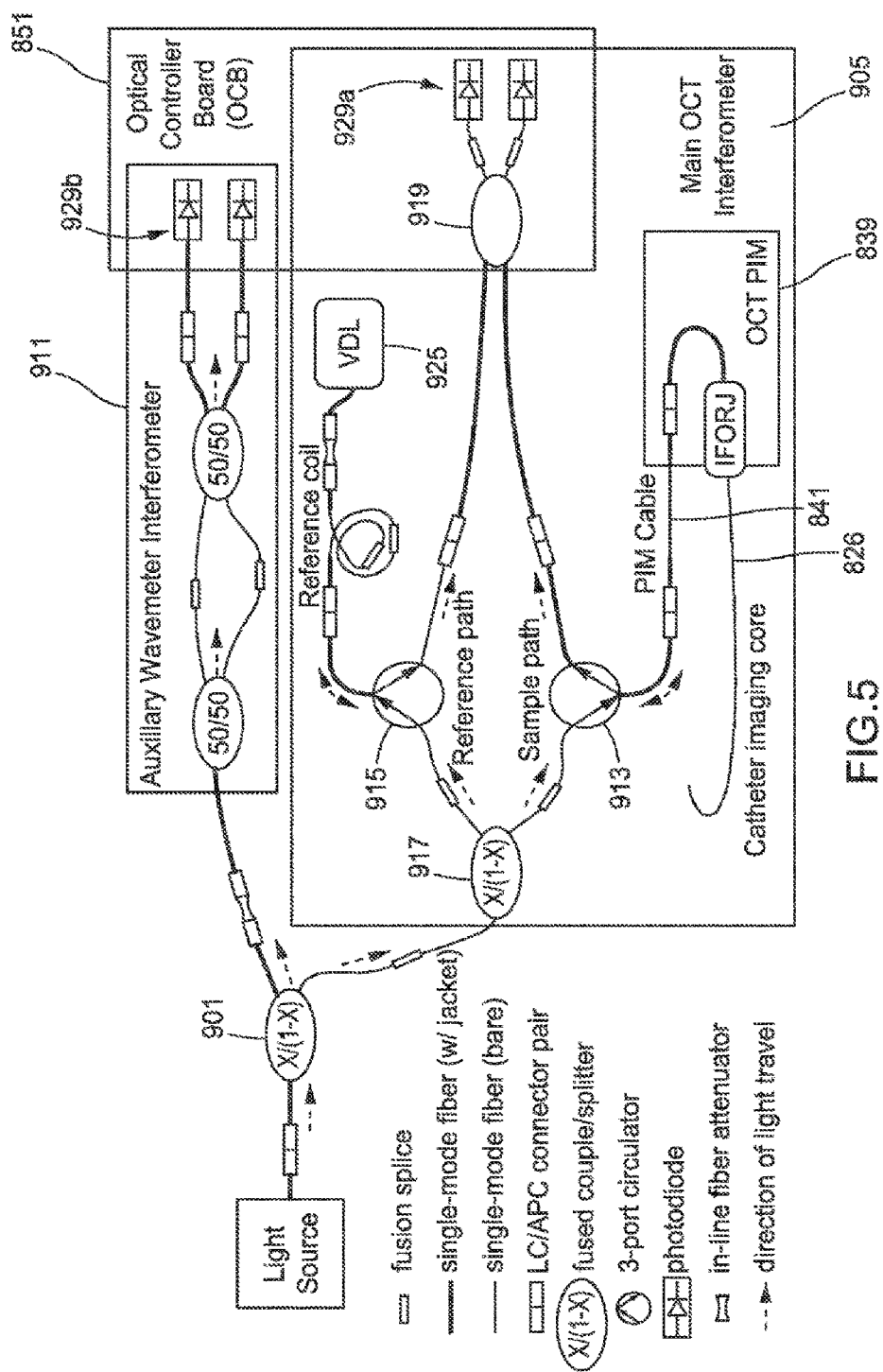
FIG. 5 is a diagram of a light path in an OCT system of certain embodiments of the invention.

FIG. 5 shows light path in a differential beam path system according to an exemplary embodiment of the invention. Light for image capture originates within the light source 827. This light is split between an OCT interferometer 905 and an auxiliary, or "clock", interferometer 911. Light directed to the OCT interferometer is further split by splitter 917 and recombined by splitter 919 with an asymmetric split ratio. The majority of the light is guided into the sample path 913 and the remainder into a reference path 915. The sample path includes optical fibers running through the PIM 839 and the imaging catheter 826 and terminating at the distal end of the imaging catheter where the image is captured.

Typical intravascular OCT involves introducing the imaging catheter into a patient's target vessel using standard interventional techniques and tools such as a guide wire, guide catheter, and angiography system. The imaging catheter may be integrated with IVUS by an OCT-IVUS system for concurrent imaging, as described in, for example, Castella et al. U.S. Patent Application Publication No. 2009/0043191 and Dick et al. U.S. Patent Application Publication No. 2009/0018393, both incorporated by reference in their entirety herein.

Figure 6:
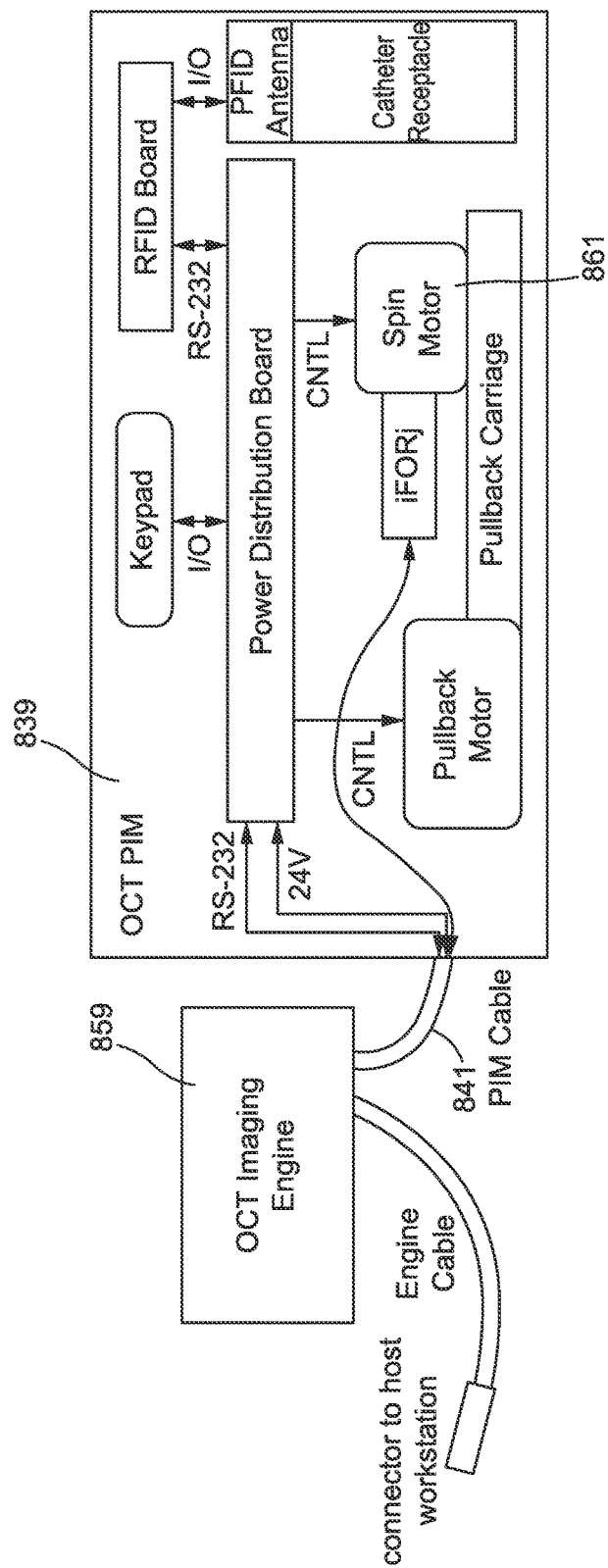
FIG. 6 is a patient interface module of an OCT system.
Figure 7:
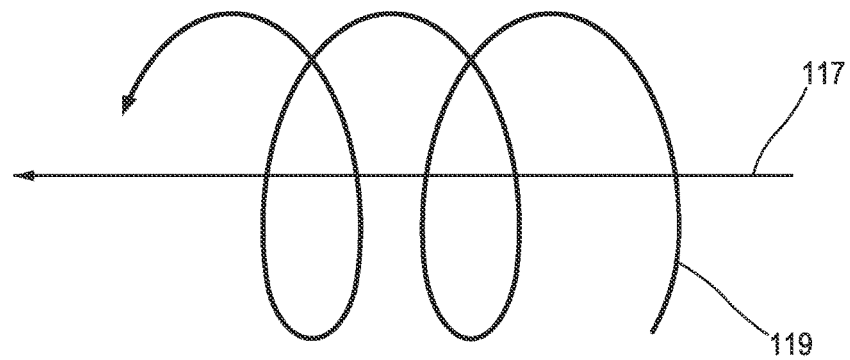
FIG. 7 is an illustration of the motion of parts of an imaging catheter according to certain embodiments of the invention.
Figure 8:
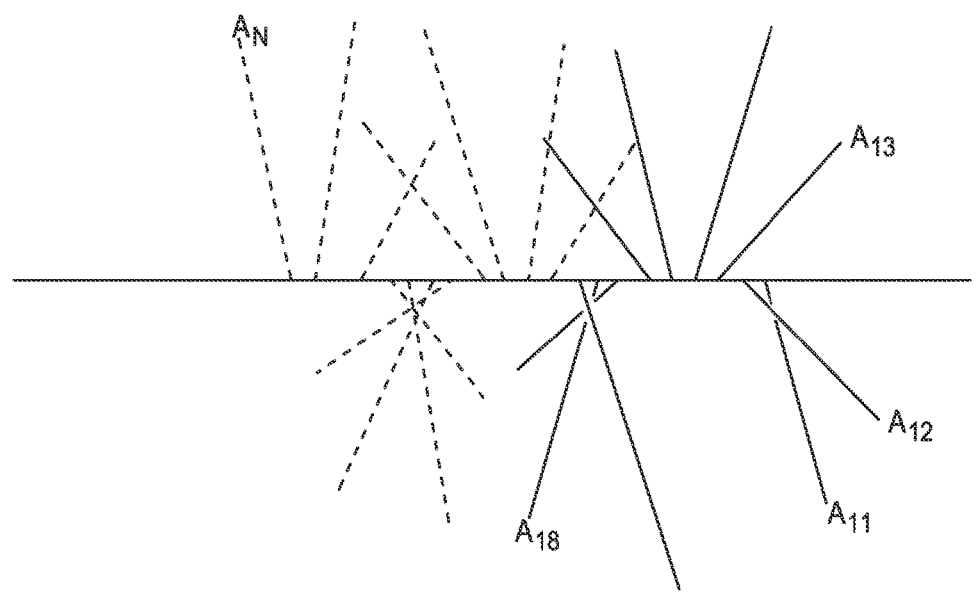
FIG. 8 shows an array of A scan lines of a three-dimensional imaging system according to certain embodiments of the invention.

Rotation of the imaging catheter is driven by spin motor 861 while translation is driven by pullback motor 865, shown in FIG. 6. This results in a motion for image capture described by FIG. 7. Blood in the vessel is temporarily flushed with a clear solution for imaging. When operation is triggered from the PIM or control console, the imaging core of the catheter rotates while collecting image data. Using light provided by the imaging engine, the inner core sends light into the tissue in an array of A-scan lines as illustrated in FIG. 8 and detects reflected light.

Figure 9:
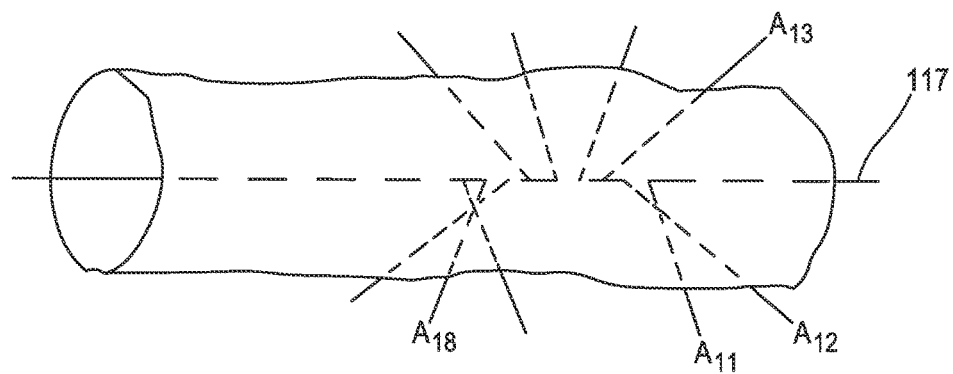
FIG. 9 shows the positioning of A scans with in a vessel.

FIG. 9 shows the positioning of A-scans within a vessel. Each place where one of A-scans A11, A12, . . . , AN intersects a surface of a feature within vessel 101 (e.g., a vessel wall) coherent light is reflected and detected. Catheter 826 translates along axis 117 being pushed or pulled by pullback motor 865.

The reflected, detected light is transmitted along sample path 913 to be recombined with the light from reference path 915 at splitter 919 (FIG. 5). A variable delay line (VDL) 925 on the reference path uses an adjustable fiber coil to match the length of reference path 915 to the length of sample path 913. The reference path length is adjusted by a stepper motor translating a mirror on a translation stage under the control of firmware or software. The free-space optical beam on the inside of the VDL 925 experiences more delay as the mirror moves away from the fixed input/output fiber.

The combined light from splitter 919 is split into orthogonal polarization states, resulting in RF-band polarization-diverse temporal interference fringe signals. The interference fringe signals are converted to photocurrents using PIN photodiodes 929a, 929b, . . . on the OCB 851 as shown in FIG. 5. The interfering, polarization splitting, and detection steps are done by a polarization diversity module (PDM) on the OCB. Signal from the OCB is sent to the DAQ 855, shown in FIG. 4. The DAQ includes a digital signal processing (DSP) microprocessor and a field programmable gate array (FPGA) to digitize signals and communicate with the host workstation and the PIM. The FPGA converts raw optical interference signals into meaningful OCT images. The DAQ also compresses data as necessary to reduce image transfer bandwidth to 1 Gbps (e.g., compressing frames with a glossy compression JPEG encoder).

Data is collected from A-scans A11, A12, . . . , AN and stored in a tangible, non-transitory memory. Typically, rotational systems consist of an imaging core which rotates and pulls back (or pushes forward) while recording an image video loop. This motion results in a three dimensional dataset of two dimensional image frames, where each frame provides a 360° slice of the vessel at different longitudinal locations.

Figure 10:
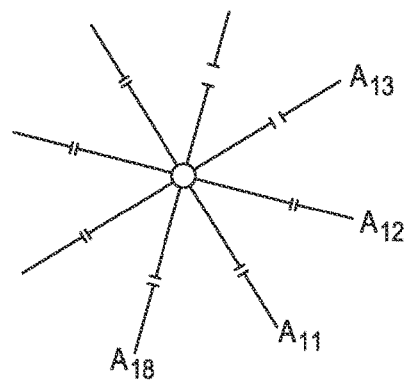
FIG. 10 illustrates a set of A scans used to compose a B scan according to certain embodiments of the invention.

A set of A-scans captured in a helical pattern 119 during one rotation of catheter 826 around axis 117 collectively define a B scan. FIG. 10 illustrates a set of A-scans A11, A12, . . . , A18 used to form a B scan according to certain embodiments of the invention. These A-scan lines are shown as would be seen looking down axis 117 (i.e., longitudinal distance between then is not shown). While eight A-scan lines are illustrated in FIG. 10, typical OCT applications can include between 300 and 1,000 A-scan lines to create a B scan (e.g., about 660). Reflections detected along each A-scan line are associated with features within the imaged tissue. Reflected light from each A-scan is combined with corresponding light that was split and sent through reference path 915 and VDL 925 and interference between these two light paths as they are recombined indicates features in the tissue.

Figure 11:
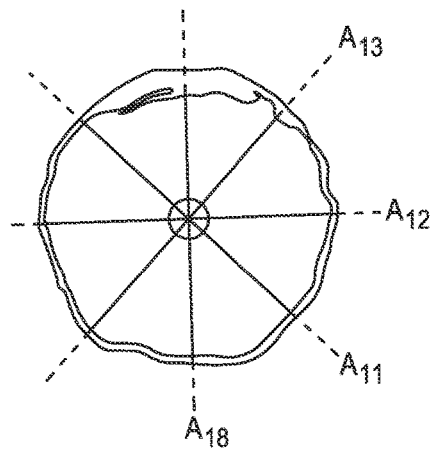
FIG. 11 shows the set of A scans shown in FIG. 10 within a cross section of a vessel.
Figure 12:
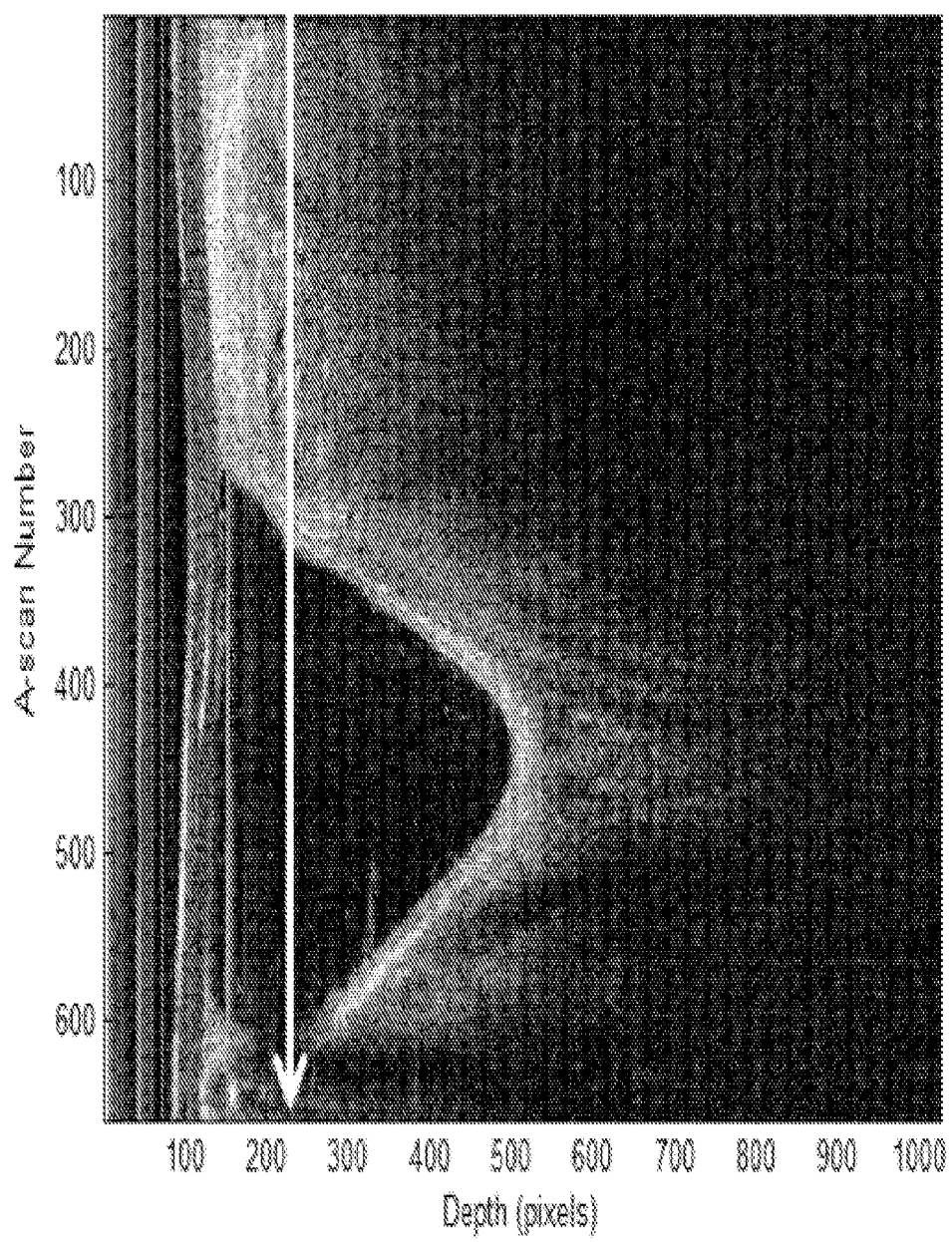
FIG. 12 shows a sample OCT B-Scan image calculated from 660 A-scans.
Figure 13:
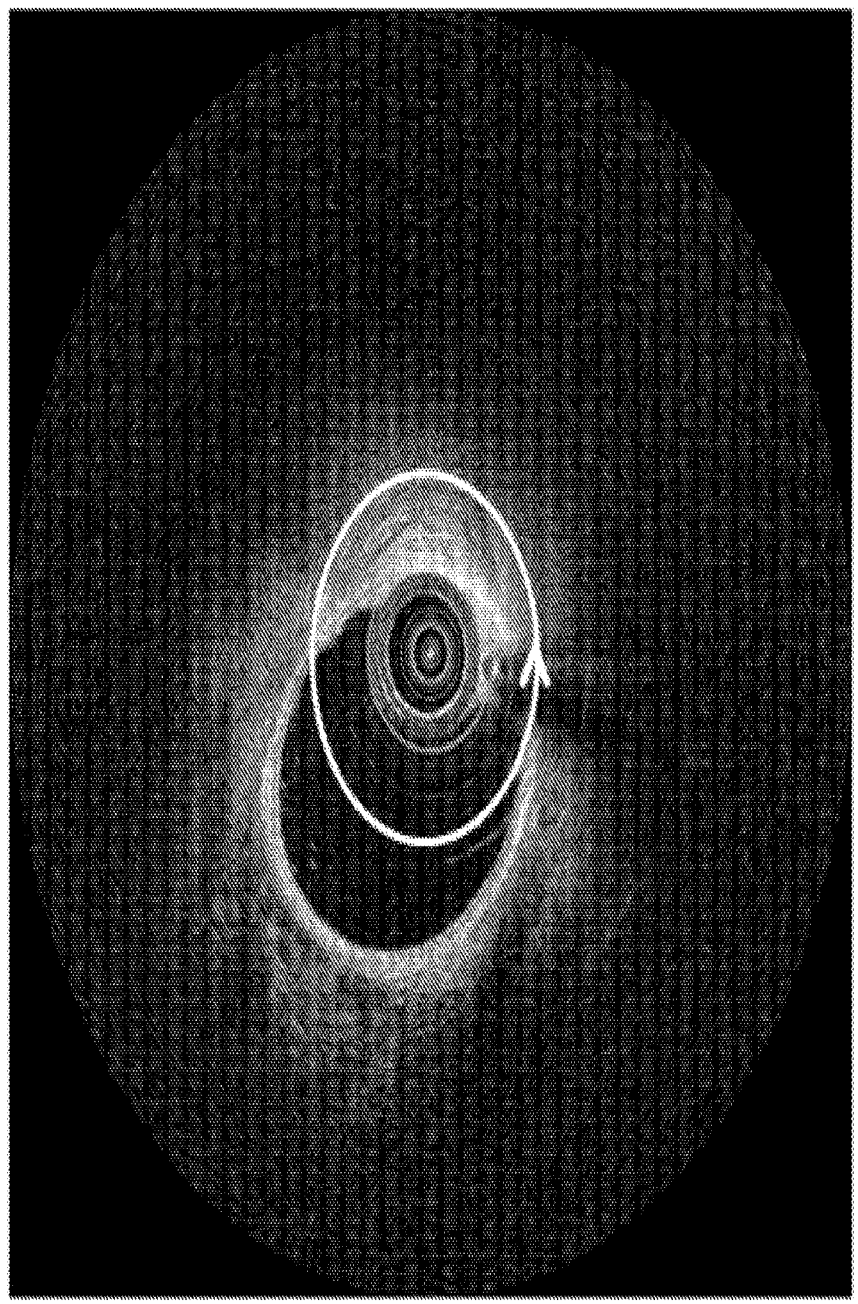
FIG. 13 shows a scan-converted OCT image from the B-scan of FIG. 14.

The data of all the A-scan lines together represent a three-dimensional image of the tissue. The data of the A-scan lines generally referred to as a B scan can be used to create an image of a cross section of the tissue, sometimes referred to as a tomographic view. For example, FIG. 11 shows the set of A-scans shown in FIG. 10 within a cross section of a vessel. The set of A-scans obtained by rotational imaging modality can be combined to form a B-scan. FIG. 12 is an example of an OCT polar coordinate B-Scan with 660 A-scans. To create a final tomographic view of the vessel, the B-scan is scan converted to a Cartesian coordinate system. FIG. 13 displays the scan converted image of the B-scan in FIG. 12.

Figure 14:
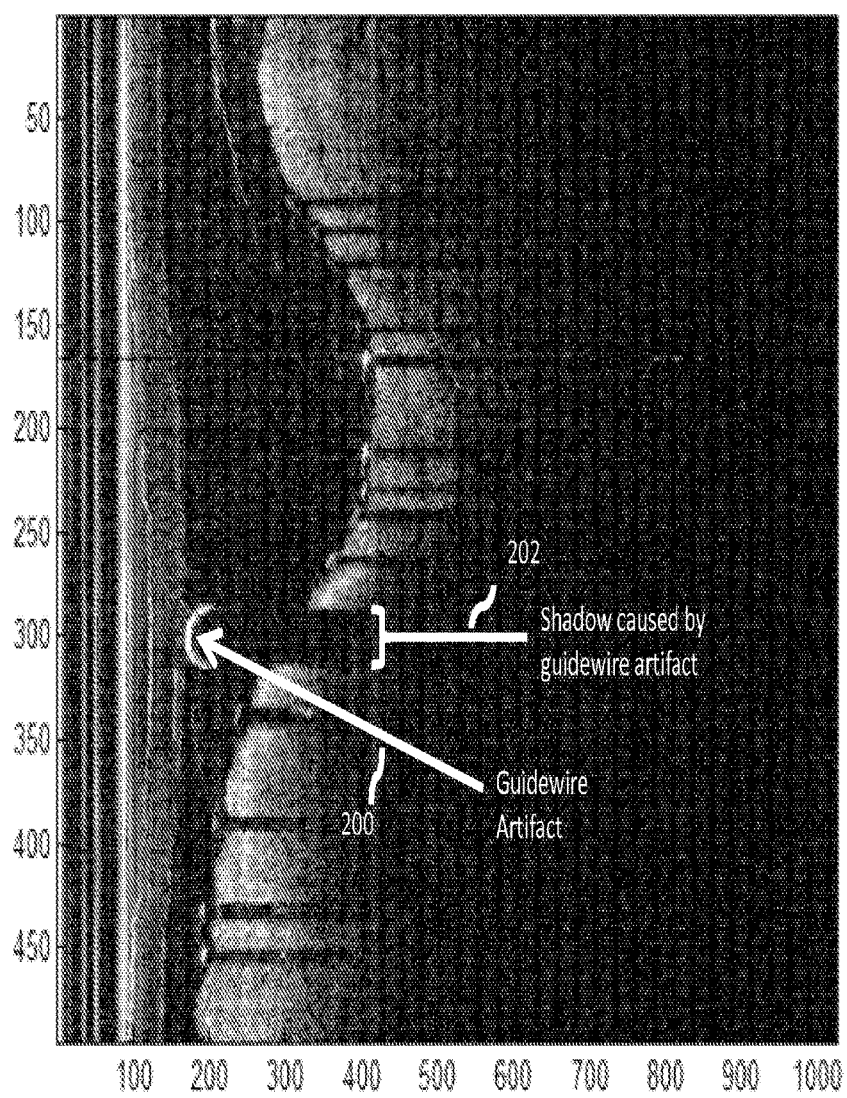
FIG. 14 shows an OCT B-scan image with a guidewire artifact and shadow highlighted.
Figure 15:
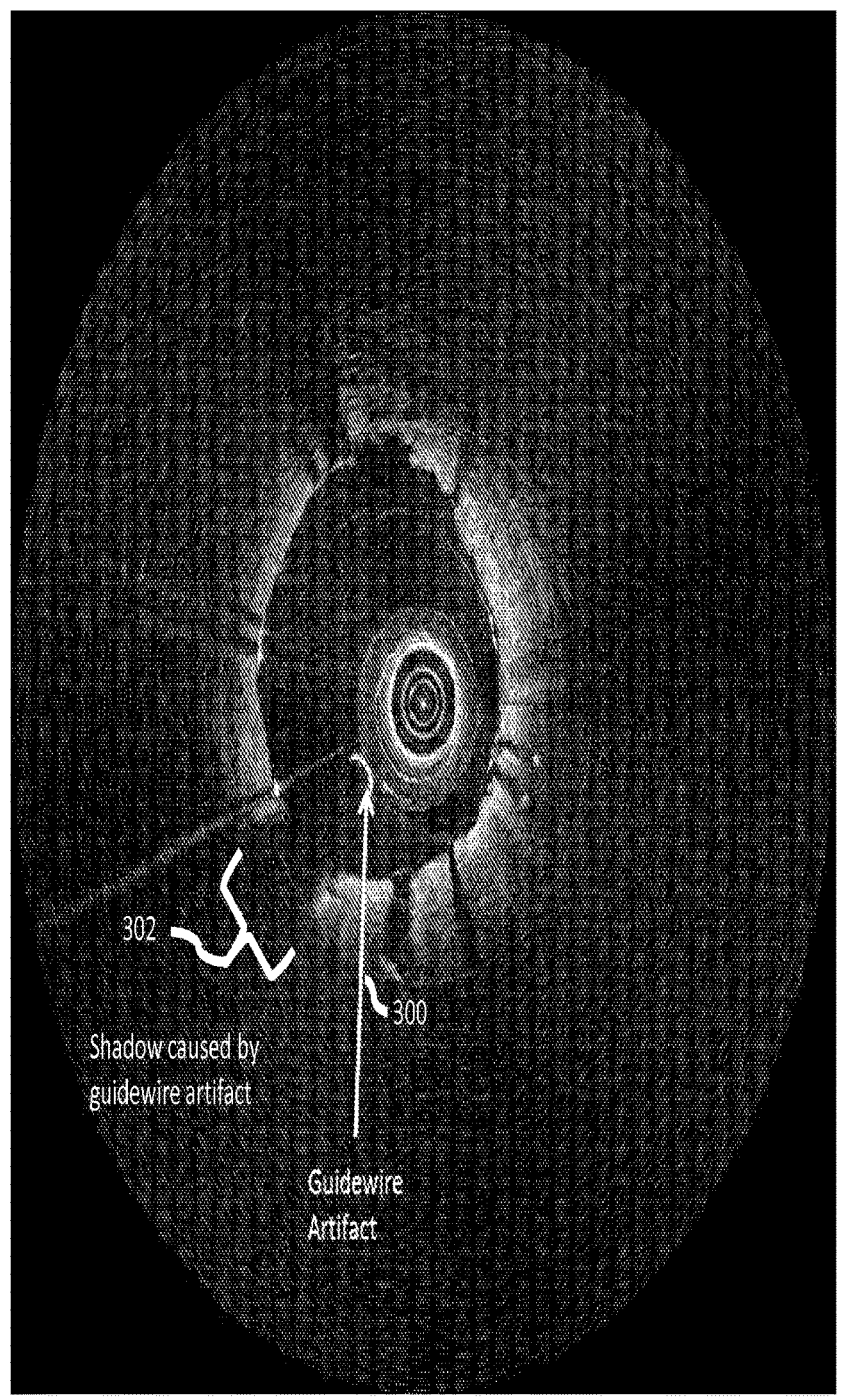
FIG. 15 shows a scan-converted OCT image with a guidewire artifact and shadow highlighted.

During acquisition of imaging data of the luminal surface that forms the A-scans, data can be lost due to the obstruction of a guidewire, or multiple guidewires. FIG. 14 depicts a B-scan image having a guidewire artifact 200 identified. Because the guidewire artifact 200 casts a shadow 202 outwardly (in a radially increasing direction) on a portion of the luminal surface and any features that would otherwise be visible on or beneath the luminal surface are obscured. FIG. 15 depicts a scan-converted image of a B-scan highlighting a guidewire artifact 300 and shadow 302 caused by the guidewire artifact 300.

Figure 16:
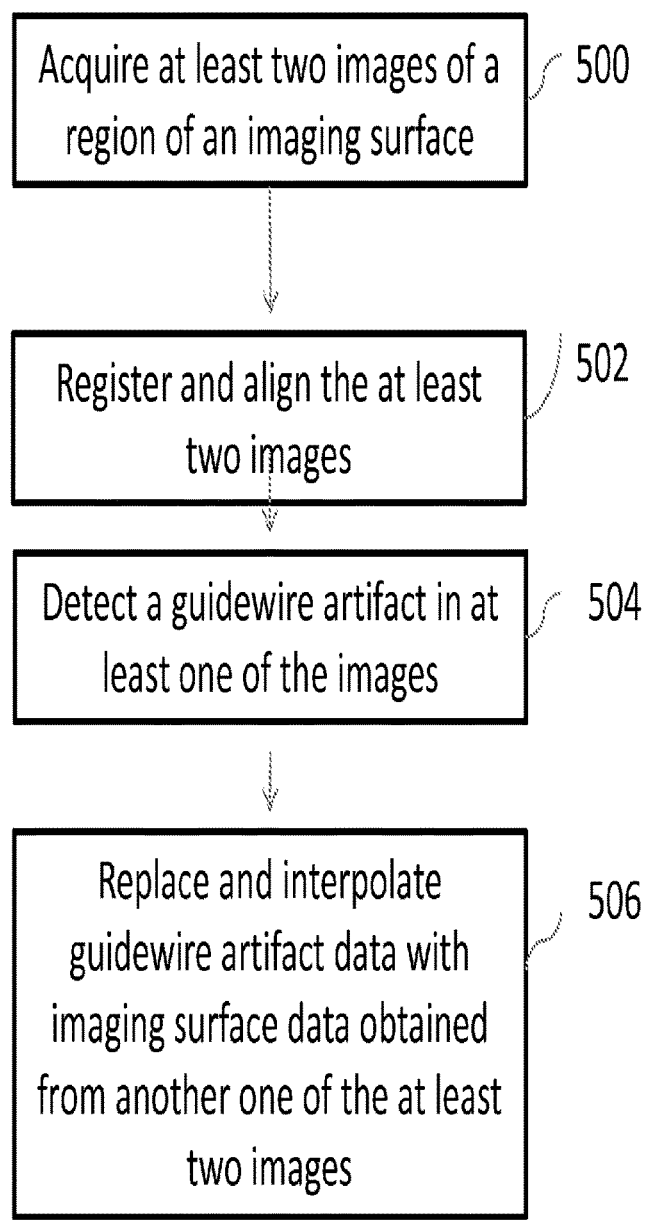
FIG. 16 depicts a block diagram for guidewire artifact removal according to embodiments of the invention.

FIG. 16 exemplifies the steps employed in aspects of the invention for removing guidewire artifacts. In step 500, at least two images are obtained of an imaging surface, in which each image is formed form an imaging data set. In step 502, the images are registered and aligned. In step 504, the guidewire artifact is detected in at least one of the images. In step 506, the data representing the guidewire artifact is replaced with data representing the imaging surface obtained from at least one other image.

In one aspect, at least two images are obtained of the same imaging surface by repeating imaging data acquisition. For example, repeating imaging pull-backs or push-forwards of the imaging catheter to obtain the desired amount of images of the same imaging region. For each repeated data acquisition of the imaging region, the guidewire is moved or rotated to different position. It should be noted that the at least two images of the imaging surface are not limited to images acquired from one imaging system, rather images can be acquired from two or more different imaging systems. For example, one data set can be obtained from an OCT imaging catheter and another dataset can be obtained from an ultrasound imaging catheter. In such embodiments, the data representing the guidewire artifact in an OCT image is replaced with data representing the luminal surface at the same location in the ultrasound image.

In step 502, the at least two images are registered and aligned to obtain the Cartesian coordinates, XYZ coordinates, of all frames and pixels in the imaging data set for each image. Image registration is the process of determining the correspondence between all points in two images of the same scene. With respect to removing the guidewire artifact, aligning the data sets allows for one to compare the position of a guidewire artifact within one imaging data set with the imaging surface at the same position in another imaging data set. This step can occur before or after step 504 without affecting the outcome of the method. Exemplary techniques for registering images are described in, for example, Joseph Hajnal, Derek Hill, and David Hawkes, editors. Medical Image Registration. CRC Press, 2001, D. I. Barnea and H. F. Silverman, "A class of algorithms for fast digital image registration", IEEE Trans. Computers, vol. 21, no. 2, pp. 179-186, 1972. For imaging data sets obtained from more than one imaging system, an exemplary technique for registering such multimodal images is described in Acharya, et al. "Image registration of multimodality 3-D medical images by chamfer matching" Proc. SPIE 1660, 356 (1992).

In one aspect, the images are registered using a phase-correlation technique. Generally, a phase-correlation technique takes two input images to produce a third imaging data set, or image, which contains a single peak. The location of this peak corresponds to the relative translation between the images. The phase correlation method is resilient to noise, occlusions, and other defects typical of medical images. Additionally, the phase-correlation uses a fast Fourier transform to compute the cross-correlation between the two images, which generally results in large performance gains. Exemplary phase-correlation registration techniques are described in Givens et al, U.S. Pat. No. 5,581,638, Dong et al, U.S. Pat. No. 6,373,970, and Reddy et al., IEEE Transaction on Image Processing, Vol. 5, No. 8 Aug. 1996.

Step 504 involves detecting a guidewire artifact within at least one of the images. Preferably, the guidewire artifact is detected in at least two of the acquired images. This allows one to determine whether the guidewire artifact is in a different location across datasets, and prevents the inadvertent substitution of data representing guidewire artifact with data representing guidewire artifact. Detecting guidewire artifact provides the Cartesian coordinates of the guidewire artifact within the imaging data set of the image. Using the Cartesian coordinates of the guidewire artifact, data representing the imaging surface in one or more of the other images sharing the same Cartesian coordinates can be obtained and used to replace the guidewire artifact.

Any method for detecting a guidewire artifact within an image can be used. For example, a guidewire can be detected using principal component analysis, such as a technique described in co-pending application entitled "Automatic Stent Detection in Intravascular Images," Begin et al. To detect a guidewire using principal component analysis, a set of pre-defined images that are known to display a guidewire are generated to train a processor to identify or recognize the guidewire in images where the guidewire location is unknown. After a training set of the pre-defined images is generated, the principal components for the set can be computed to create an object space for the guidewire. By projecting an input image with an unknown guidewire location onto the object space, the guidewire can be detected within the input image. In another aspect, a guidewire artifact can be detected within an input image by generating a training set of images of a guidewire, where each image is defined by one or more features. A covariance matrix can be computed for a feature within each pre-defined image of the training set. The covariance for a feature within the input image can be calculated and compared to the covariances of the training set. From the comparison, the guidewire can be detected within the input image.

A further exemplary method for detection of a guidewire artifact utilizes the opaque nature of the guidewire by employing an edge detector or ridge detector as known in the art to detect the guidewire shadow artifact projected by a guidewire. Because the guidewire are often made of light-blocking material such as metal, the shadow in the surrounding tissue has a sharp edge in which the transition length is approximately equal to the lateral resolution of the imaging system. A shadow can be viewed as the inverted ridge (valley) amid surrounding tissues because it is usually the local intensity minima and it is substantially vertically oriented. Ridge-detecting filters are applied to the original image to obtain the ridge intensity level map. The ridge intensity at each scan or horizontal location is averaged in the vertical direction to generate the ridge intensity profile image or map. The average intensities of this map are then graphed and the peaks in the graph are detected. The peaks correspond to the location of the centers of the guidewire artifacts. The guidewire artifact can also be detected directly by using its bright ridge-like features. Information useful in implementing the ridge detector method exemplified may be found, for example, in Xu, U.S. Patent Publication No. 2010/0094127.

Another technique for detecting guidewire artifacts includes first detecting the lumen border and then detecting the artifact based on the intensity of pixels along the lumen border. This technique is described in detail in relation to stent strut shadows, in Unal et al., U.S. Pat. No. 7,801,343. Detection of the lumen boundary may be accomplished, for example, by evolving a geometric shape, such as an ellipse, using a region-based algorithm technique, a geodesic boundary-based algorithm technique or a combination of the two techniques. The intensities of the pixels along lumen border are then used to detect the presence and location of the guidewire shadow in the image.

An additional suitable technique for detecting the guidewire artifact is described in Kimmel et al., U.S. Pat. No. 7,397,935. This method examines each A-scan within a rotation spanning 360 degrees to determine which of the a-scans includes the guidewire artifact and/or shadow artifact. For example, a guidewire artifact 202 can be detected across A-scans by comparing the brightness of the brightest portion of data in an A-scan and a standard deviation of the brightness in the rest of the A-scan. A-scans that include a guidewire have a maximum difference between the brightest portion of data at the bottom of the A-scan and the standard deviation of brightness. Information useful in implementing this exemplary method may be found, for example, in Kimmel et al. U.S. Pat. No. 7,397,935.

After the position of the guidewire artifact is known, the data representing the guidewire artifact in one image is replaced with data representing the imaging surface in another imaging image. The data representing the imaging surface can be taken from one or more other images. In certain aspects, the resulting image with the guidewire artifact removed is then interpolated to enhance image quality using any method of interpolation known in the art. Suitable interpolation techniques include, for example, liner interpolation, cubic interpolation, and nearest neighbor interpolation, and are described in Bankman, Handbook of Medical Imaging: Processing and Analysis (2000).

In certain aspects, the acquired images may have more than one guidewire artifact present. For example, combined OCT and ultrasound imaging techniques may have a guidewire for the OCT imaging catheter and a guidewire for the ultrasound imaging catheter. In order to remove multiple guidewires present in an image, embodiments of the invention are repeated for each guidewire. For example, removal of multiple guidewires is accomplished by acquiring images of an imaging surface having two or guidewires moved to different locations, registering the two or more images, detecting the guidewires in one or more images, replacing the detected guidewires in one image with data representing the imaging surface at the same location in one or more other images.

In some embodiments, a device of the invention includes an OCT imaging system and obtains a three-dimensional data set through the operation of OCT imaging hardware. In some embodiments, a device of the invention is a computer device such as a laptop, desktop, or tablet computer, and obtains a three-dimensional data set by retrieving it from a tangible storage medium, such as a disk drive on a server using a network or as an email attachment.

Methods of the invention can be performed using software, hardware, firmware, hardwiring, or combinations of any of these. Features implementing functions can also be physically located at various positions, including being distributed such that portions of functions are implemented at different physical locations (e.g., imaging apparatus in one room and host workstation in another, or in separate buildings, for example, with wireless or wired connections).

Figure 17:
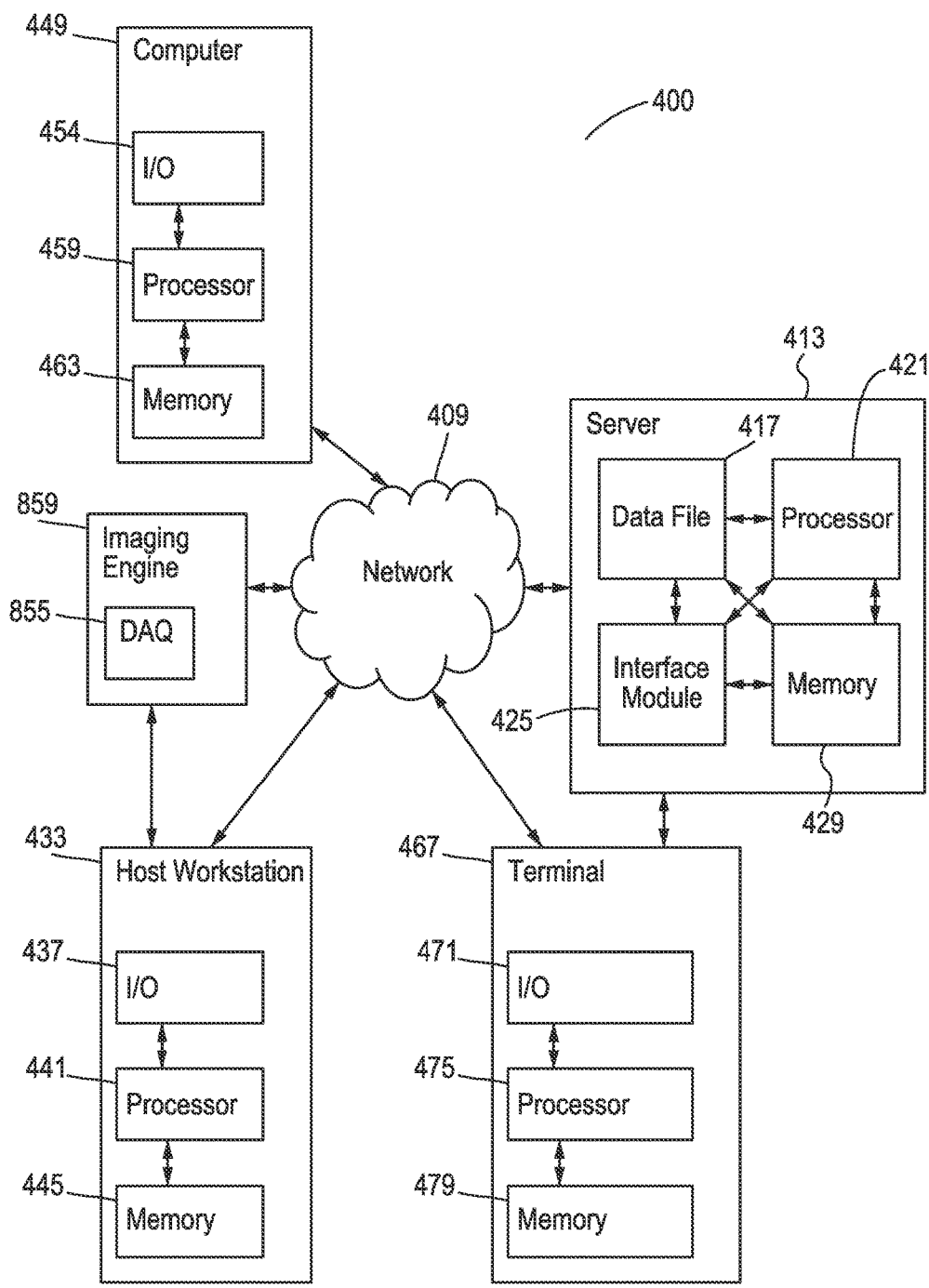
FIG. 17 is a system diagram according to certain embodiments.

In some embodiments, a user interacts with a visual interface to view images from the imaging system. Input from a user (e.g., parameters or a selection) are received by a processor in an electronic device. The selection can be rendered into a visible display. An exemplary system including an electronic device is illustrated in FIG. 17. As shown in FIG. 17, imaging engine 859 communicates with host workstation 433 as well as optionally server 413 over network 409. In some embodiments, an operator uses computer 449 or terminal 467 to control system 400 or to receive images. An image may be displayed using an I/O 454, 437, or 471, which may include a monitor. Any I/O may include a keyboard, mouse or touchscreen to communicate with any of processor 421, 459, 441, or 475, for example, to cause data to be stored in any tangible, nontransitory memory 463, 445, 479, or 429. Server 413 generally includes an interface module 425 to effectuate communication over network 409 or write data to data file 417.

Processors suitable for the execution of computer program include, by way of example, both general and special purpose microprocessors, and any one or more processor of any kind of digital computer. Generally, a processor will receive instructions and data from a read-only memory or a random access memory or both. The essential elements of computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, solid state drive (SSD), and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having an I/O device, e.g., a CRT, LCD, LED, or projection device for displaying information to the user and an input or output device such as a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back-end component (e.g., a data server 413), a middleware component (e.g., an application server), or a front-end component (e.g., a client computer 449 having a graphical user interface 454 or a web browser through which a user can interact with an implementation of the subject matter described herein), or any combination of such back-end, middleware, and front-end components. The components of the system can be interconnected through network 409 by any form or medium of digital data communication, e.g., a communication network. Examples of communication networks include cell network (e.g., 3G or 4G), a local area network (LAN), and a wide area network (WAN), e.g., the Internet.

The subject matter described herein can be implemented as one or more computer program products, such as one or more computer programs tangibly embodied in an information carrier (e.g., in a non-transitory computer-readable medium) for execution by, or to control the operation of, data processing apparatus (e.g., a programmable processor, a computer, or multiple computers). A computer program (also known as a program, software, software application, app, macro, or code) can be written in any form of programming language, including compiled or interpreted languages (e.g., C, C++, Perl), and it can be deployed in any form, including as a stand-alone program or as a module, component, subroutine, or other unit suitable for use in a computing environment. Systems and methods of the invention can include instructions written in any suitable programming language known in the art, including, without limitation, C, C++, Perl, Java, ActiveX, HTML5, Visual Basic, or JavaScript.

A computer program does not necessarily correspond to a file. A program can be stored in a portion of file 417 that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

A file can be a digital file, for example, stored on a hard drive, SSD, CD, or other tangible, non-transitory medium. A file can be sent from one device to another over network 409 (e.g., as packets being sent from a server to a client, for example, through a Network Interface Card, modem, wireless card, or similar).

Writing a file according to the invention involves transforming a tangible, non-transitory computer-readable medium, for example, by adding, removing, or rearranging particles (e.g., with a net charge or dipole moment into patterns of magnetization by read/write heads), the patterns then representing new collocations of information about objective physical phenomena desired by, and useful to, the user. In some embodiments, writing involves a physical transformation of material in tangible, non-transitory computer readable media (e.g., with certain optical properties so that optical read/write devices can then read the new and useful collocation of information, e.g., burning a CD-ROM). In some embodiments, writing a file includes transforming a physical flash memory apparatus such as NAND flash memory device and storing information by transforming physical elements in an array of memory cells made from floating-gate transistors. Methods of writing a file are well-known in the art and, for example, can be invoked manually or automatically by a program or by a save command from software or a write command from a programming language.

What is claimed is:

1. A computer-readable, non-transitory, medium storing software code representing instructions that when executed by a computing system cause the computing system to perform a method of removing a guidewire artifact, the method comprising:

acquiring at least two intravascular images of an imaging surface using a rotating transducer or probe movable relative to a guidewire, each image comprising a set of data associated with the same imaging modality and associated with the imaging surface having the guidewire moved to a different position;

registering and aligning the at least two intravascular images;

detecting a guidewire artifact present in at least one of the at least two intravascular images, wherein the detecting comprises determining the coordinates of the artifact in the at least one of the at least two intravascular images; and replacing the guidewire artifact in the at least one of the at least two intravascular images with data representing the imaging surface obtained from at least one other image of the at least two intravascular images.

2. The computer-readable, non-transitory medium of claim 1, wherein the images are automatically registered.

3. The computer-readable, non-transitory medium of claim 1, wherein the images are registered using the phase correlation method.

4. The computer-readable, non-transitory medium of claim 1, wherein the guidewire artifact present in the at least one of the at least two intravascular images shares the same three-dimensional Cartesian coordinates as the data representing the portion of the imaging surface obtained from at least one other image of the at least two intravascular images.

5. The computer-readable, non-transitory medium of claim 1, wherein the images are acquired using optical coherence tomography, ultrasound technology, intravascular spectroscopy, or photo-acoustic tomography.

6. A system for imaging and removing a guidewire artifact, comprising:
   a central processing unit (CPU); and
   a storage device coupled to the CPU and having stored there information for configuring the CPU to:
      acquire at least two intravascular images of an imaging surface using a rotating transducer or probe movable relative to a guidewire, each image comprising a set of data associated with the same imaging modality and associated with the imaging surface having the guidewire moved to a different position;
      register and align the at least two intravascular images;
      detect a guidewire artifact present in at least one of the at least two intravascular images, wherein the detecting comprises determining the coordinates of the artifact in the at least one of the at least two intravascular images; and
      replace the guidewire artifact in the at least one of the at least two intravascular images with data representing the imaging surface obtained from at least one other image of the at least two intravascular images.

7. The system of claim 6, wherein the images are automatically registered.

8. The system of claim 6, wherein the images are registered using the phase correlation method.

9. The system of claim 6, wherein the data defines a Cartesian coordinate system and the guidewire artifact present in the image shares the same Cartesian coordinates as the data representing the imaging surface obtained from at least one other image of the at least two intravascular images.

10. The system of claim 6, wherein the images are acquired using optical coherence tomography, ultrasound technology, intravascular spectroscopy, or photoacoustic tomography.

11. The system of claim 6, wherein storage device has information stored there for further configuring the CPU to:
   determine size and position within the Cartesian coordinate system of an object causing the artifact.

12. A method of removing an imaging artifact, the method comprising:
   acquiring a first intravascular image of an imaging surface using a rotating transducer or probe in a first position relative to a guidewire;
   acquiring a second intravascular image of the imaging surface using the rotating transducer or probe in a second position relative to the guidewire, the first and second intravascular images associated with the same imaging modality;
   registering and aligning the at least two intravascular images;
   detecting an artifact present in one of the first or second intravascular images, wherein the detecting comprises determining the coordinates of the artifact in the at least one of the first or second intravascular images; and
   replacing the artifact in the at least one of the first or second intravascular images with data representing the imaging surface obtained from the other image of the first or second intravascular images.

* * * * *